(12) United States Patent
Ferrando et al.

(10) Patent No.: US 8,633,179 B2
(45) Date of Patent: Jan. 21, 2014

(54) SYNERGISTIC INTERACTION OF NOTCH-1 INHIBITORS WITH GLUCOCORTICOIDS

(75) Inventors: Adolfo A. Ferrando, New York, NY (US); Pedro J. Real, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1009 days.

(21) Appl. No.: 12/450,131

(22) PCT Filed: Mar. 13, 2008

(86) PCT No.: PCT/US2008/003268
§ 371 (c)(1),
(2), (4) Date: Dec. 18, 2009

(87) PCT Pub. No.: WO2008/112249
PCT Pub. Date: Sep. 18, 2008

(65) Prior Publication Data
US 2010/0093684 A1    Apr. 15, 2010

Related U.S. Application Data

(60) Provisional application No. 60/906,912, filed on Mar. 13, 2007, provisional application No. 61/002,957, filed on Nov. 12, 2007.

(51) Int. Cl.
*A61K 31/56* (2006.01)
(52) U.S. Cl.
USPC ............ 514/171; 514/177; 514/179; 514/180
(58) Field of Classification Search
USPC .......................................................... 514/171
See application file for complete search history.

(56) References Cited

U.S. PATENT DOCUMENTS

| | | | |
|---|---|---|---|
| 6,653,303 B1 * | 11/2003 | Wu et al. ...................... | 514/220 |
| 2003/0032673 A1 * | 2/2003 | Nagy ........................... | 514/557 |

OTHER PUBLICATIONS

Micchelli, "γ-Secretase/presenilin inhibitors for Alzheimers disease phenocoy Notch mutation in *Drosophila*", the FASEB Journal, vol. 17, Jan. 2003, pp. 79-81.*
Marin, Dementia and Geriatric Cognitive disorders 1996, vol. 7, No. 4 (abstract only).*
Hotchkiss et al. "Fluticasone Propionate Attenuates Ozone-induced Rhinitis and Mucous Cell Metaplasia in Rat Nasal..," Am. J. Respir. Cell Mol. Biol. 1998, vol. 18, pp. 91-99.
Van Es, et al. "Notch Secretase Inhibition Turns Proliferative Cells in Intestinal Crypts and Adenomas into Goblet Cells," Nature Jun. 2005, vol. 435, pp. 959-963.
O'Neil, et al. "Activating Notch1 Mutations in Mouse Models of T-ALL," Neoplasia, Jan. 2006, vol. 107, pp. 781-785.
Morohashi, et al. "C-terminal Fragment of Presenilin is the Molecular Target of a Dipeptidic ...," Journal of Biological Chemistry, 2006, vol. 281, No. 21 pp. 14670-14676.

* cited by examiner

*Primary Examiner* — San-Ming Hui
(74) *Attorney, Agent, or Firm* — Bryan Cave LLP

(57) ABSTRACT

The present invention relates to methods and compositions for preventing and/or treating various conditions in a patient, including for example, T-cell lymphoblastic leukemia and lymphoma as well as neurodegenerative diseases, such as for example, Alzheimer's disease. In one preferred embodiment of the invention, such methods include providing a patient with an effective amount of a combination of a NOTCH-1 inhibitor and glucocorticoid. The present invention further encompasses methods for increasing the efficacy of, and mitigating resistance to, glucocorticoids in the treatment of T-cell lymphoblastic leukemia and lymphoma, which generally include providing a patient with an effective amount of one or more NOTCH-1 inhibitors.

14 Claims, 21 Drawing Sheets

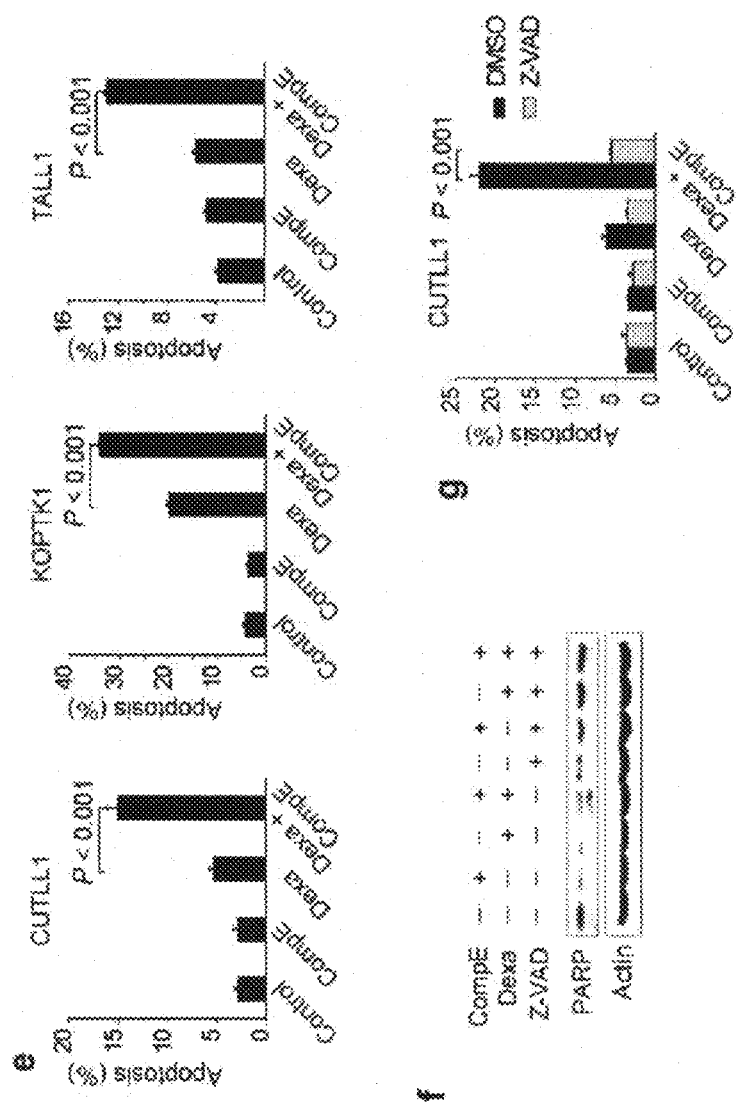
Figure 1 (con't)

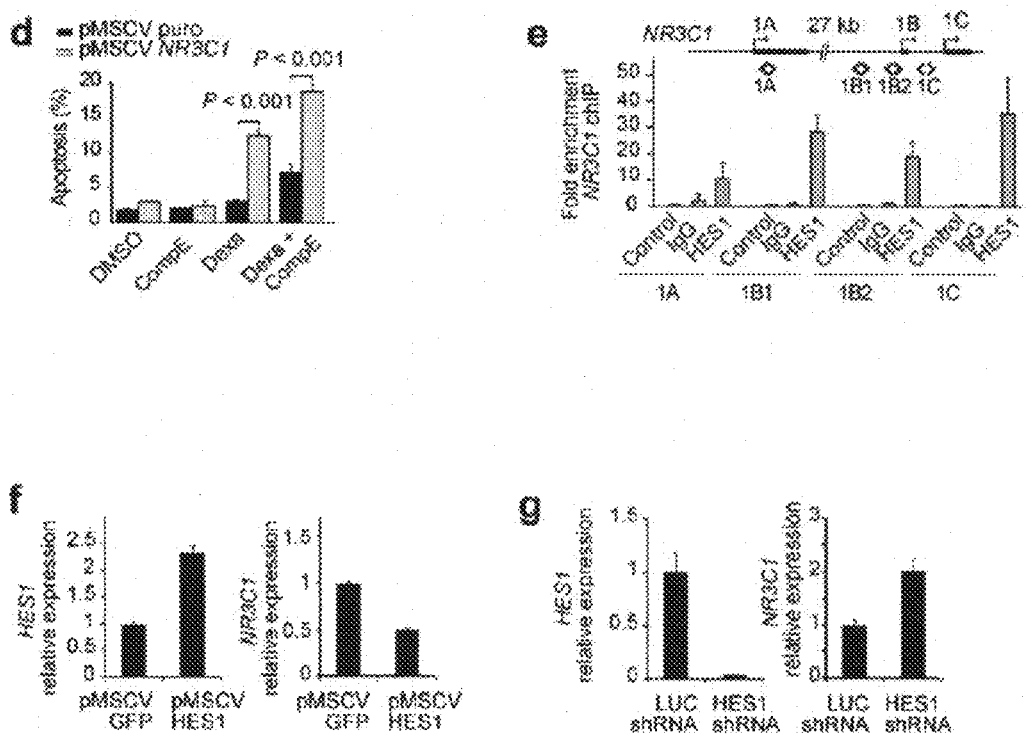
Figure 2 (con't)

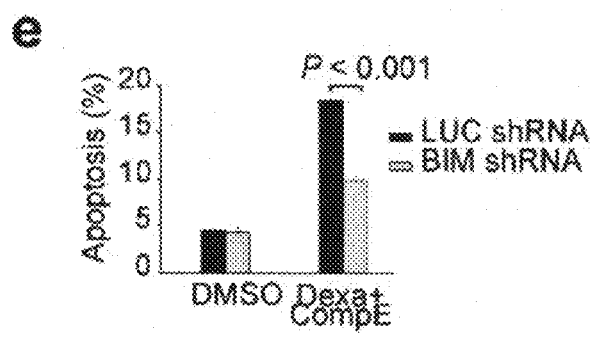
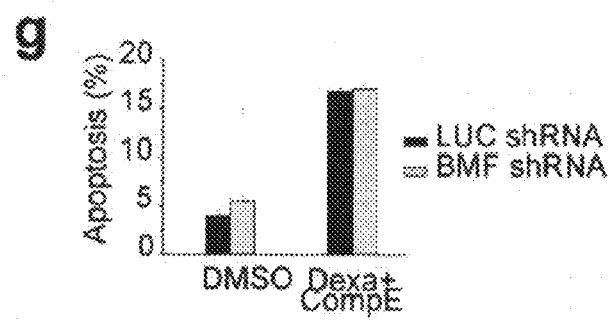
Figure 3 (con't)

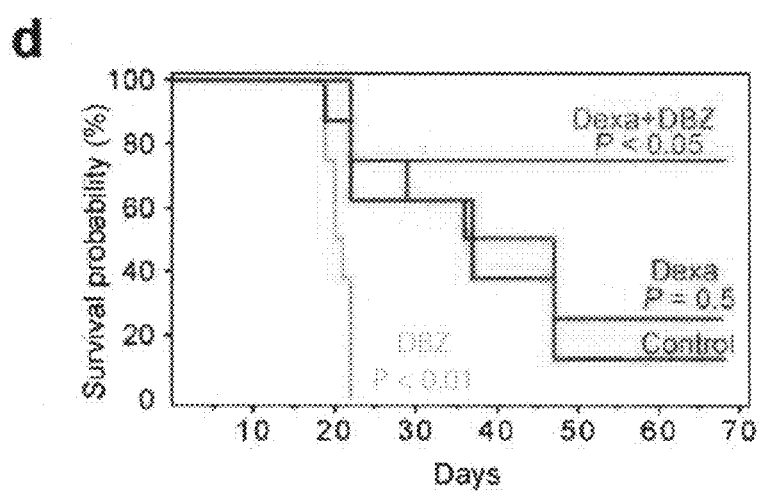
Figure 4 (con't)

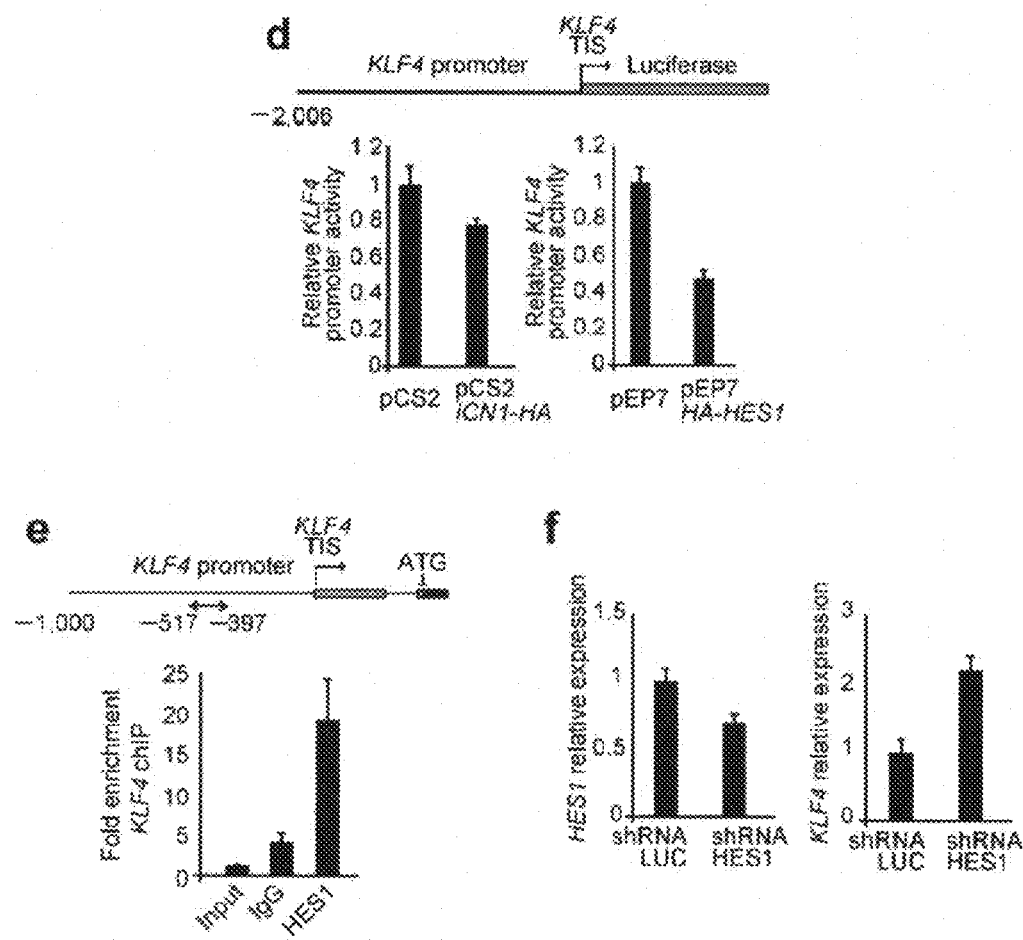
Figure 6 (con't)

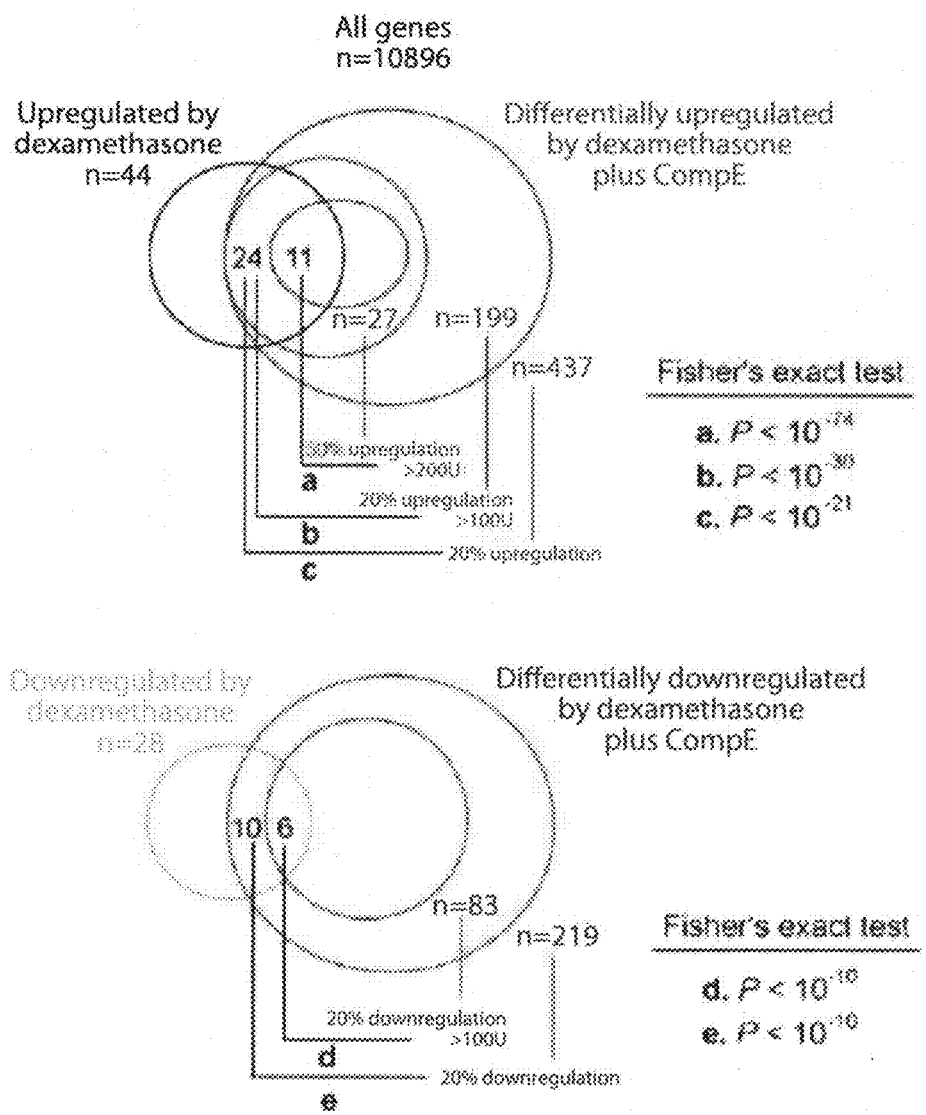
Figure 8 (con't)

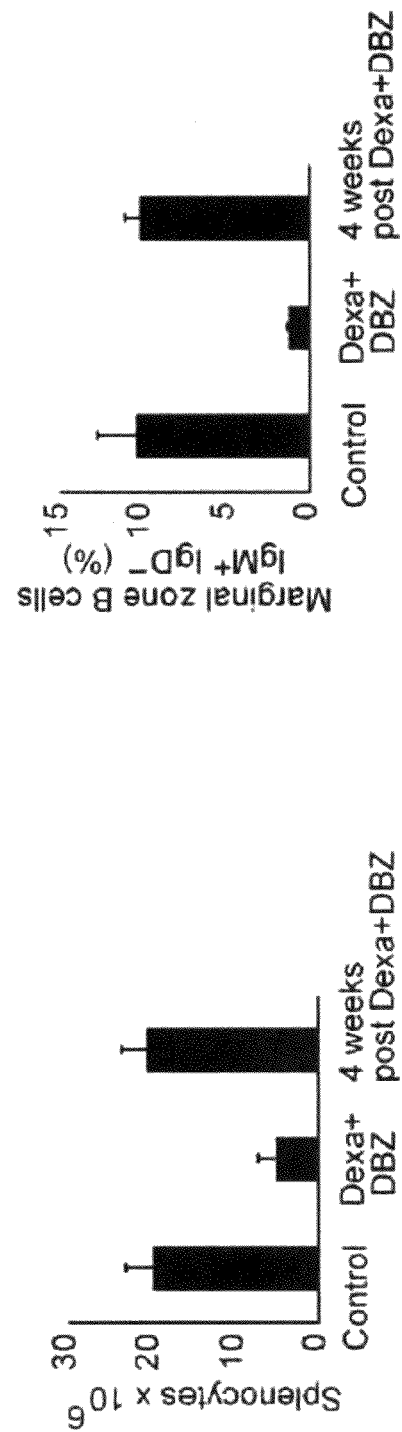
Figure 13 (con't)

SEQUENCE LISTING

<160> NUMBER OF SEQ ID NOS: 4

<210> SEQ ID NO 1
<211> LENGTH: 19
<212> TYPE: DNA

```
<213> ORGANISM: Artificial
<220> FEATURE:
<223> OTHER INFORMATION: shRNA sequence

<400> SEQUENCE: 1
gacagcatct gagcacaga                                              19

<210> SEQ ID NO 2
<211> LENGTH: 21
<212> TYPE: DNA
<213> ORGANISM: Artificial
<220> FEATURE:
<223> OTHER INFORMATION: shRNA sequence.

<400> SEQUENCE: 2
aaggtagaca attgcagcct g                                           21

<210> SEQ ID NO 3
<211> LENGTH: 21
<212> TYPE: DNA
<213> ORGANISM: Artificial
<220> FEATURE:
<223> OTHER INFORMATION: shRNA sequence.

<400> SEQUENCE: 3
gcccagagta aggaatgtct t                                           21

<210> SEQ ID NO 4
<211> LENGTH: 21
<212> TYPE: DNA
<213> ORGANISM: Artificial
<220> FEATURE:
<223> OTHER INFORMATION: shRNA sequence.

<400> SEQUENCE: 4
cctaaggtta agtcgccctc g                                           21
```

SYNERGISTIC INTERACTION OF NOTCH-1 INHIBITORS WITH GLUCOCORTICOIDS

CROSS-REFERENCE TO RELATED APPLICATIONS

This application is a U.S. National Stage Application under 35 USC §371 of International Application No. PCT/2008/03268, which was filed on Mar. 13, 2008, which claims benefit to U.S. Provisional Application No. 60/906,912, filed Mar. 13, 2007, and U.S. Provisional Application No. 61/002,957, filed Nov. 12, 2007, all of which are incorporated by reference in their entireties as if recited in full herein.

FIELD OF THE INVENTION

The field of the present invention relates to methods and compositions for preventing, treating, and/or ameliorating the effects of various conditions in a mammal, such as cancer and Alzheimer's disease.

BACKGROUND OF THE INVENTION

Molecularly targeted therapies directed against signaling pathways that control cell growth, proliferation and differentiation in malignant lymphoblasts have recently emerged as promising tools in the therapy of human leukemias. In this regard, the identification of activating mutations in the NOTCH-1 receptor in over 50% of human T-cell acute lymphoblastic leukemias (T-ALL) has prompted the initiation of clinical trials to test the effectiveness of drugs inhibiting NOTCH-1 signaling in this disease.

The NOTCH signaling pathway is a critical regulator of cell fate, specification, and stem cell homeostasis in the hematopoietic system. There are three fundamental components of the NOTCH pathway: the DSL ligands (Delta-like 1, 3 and 4; and Jagged 1 and 2), the NOTCH receptors (NOTCH-1-4), and the CSL DNA binding protein, a transcription factor that interacts with the activated form of NOTCH receptors and mediates the conversion of NOTCH-activating signals at the cell surface into changes in gene expression in the nucleus.

Mature NOTCH receptors are generated from a precursor polypeptide that is post-translationally cleaved into two fragments by a furin protease during its maturation in the trans-Golgi network. In the resting receptor, these two fragments interact to form a heterodimeric transmembrane protein. Upon binding to its ligands, the transmembrane portion of NOTCH-1 is sequentially cleaved first by an ADAM protease and then by the γ-secretase complex. This final endomembrane cleavage step releases the active intracellular fragment of NOTCH-1 (ICN1), which translocates to the nucleus and activates target gene expression by forming a ternary complex with the CSL DNA-binding protein and the MAML1 transcriptional coactivator. Importantly, the presenilin γ-secretase complex also has a pathogenic role in Alzheimer's disease, fostering the development of highly active γ-secretase inhibitors (GSIs) for the treatment of this neurodegenerative disease.

GSIs effectively inhibit the last proteolytic cleavage required for the activation of the NOTCH-1 receptor and have been shown to induce cell cycle arrest in T-ALL cell lines in vitro. The cytostatic effects of GSIs seem to be mediated by the down regulation of a transcriptional regulatory network controlling macromolecular metabolism, cell growth and proliferation downstream of NOTCH-1 in T-ALL. Activation of NOTCH receptors has also been implicated in the pathogenesis of numerous solid tumors, including breast and ovarian carcinomas and medulloblastoma, thereby supporting a possible role for GSI's in the treatment of solid tumors.

Glucocorticoids (GCs) are a group of bioactive molecules capable of binding the glucocorticoid receptor (GR) and encompass cortisol, a natural hormone, and a number of structurally related compounds. In resting conditions, the glucocorticoid receptor is located in the cytosol, in close association with inactivating heat shock proteins. Binding to glucocorticoids induces conformational changes that release the GR from heat shock proteins, induce its dimerization and promote translocation to the nucleus where it binds to DNA and regulates the expression of target genes. In addition to this direct role as a ligand-activated transcriptional regulator, the GR also affects gene expression by inhibiting the activity of other transcription factors such as AP1 and NFκB.

Physiologic glucocorticoid signaling plays important roles in the regulation of immune responses and the generation of the immune repertoire. However, pharmacologic doses of glucocorticoids induce cell cycle arrest and apoptosis in normal lymphocytes and have direct anti-cancer activity against lymphoid malignancies. Indeed, glucocorticoids have been used in the treatment of lymphoid tumors since the early days of chemotherapy and constitute part of the core treatment for acute lymphoblastic leukemia (ALL). The response rates to glucocorticoid monotherapy in primary pediatric acute lymphoblastic leukemia range between 45 and 65%. However, after relapse the rate of subsequent remission induction with glucocorticoids alone falls to 25%. The importance of glucocorticoids in the treatment of ALL is emphasized by the excellent prognosis associated with in vivo early response to glucocorticoid therapy. In contrast, ALL patients whose lymphoblasts show in vitro resistance to glucocorticoid-induced apoptosis have a less favorable prognosis.

Although the specific mechanisms that mediate glucocorticoid induced cell death and glucocorticoid resistance are not fully understood, several lines of evidence support that the mitochondrial/intrinsic cell death pathway mediates glucocorticoid induced apoptosis.

Activation of the GR induces the expression of the pro-apoptotic BH3-only gene BIM in ALL cells and both BIM and PUMA, a second pro-apoptotic BH3-only factor, are necessary for appropriate GC-induced apoptosis. Conversely, lymphocytes from double knockout $Bax^{-/-}$ $Bak^{-/-}$ mice, which have a complete block in the intrinsic apoptotic pathway, are resistant to glucocorticoid-induced apoptosis. Finally, high-level expression of the anti-apoptotic factor MCL1 has been correlated with glucocorticoid resistance in vitro, and turning the balance of pro-apoptotic and anti-apoptotic factors towards cell survival by BCL2 or MCL1 overexpression can protect lymphoblastic leukemia cells from GC-induced programmed cell death.

Enthusiasm for GSIs in the treatment of T-ALL, however, is often tempered by the apparent inability of these drugs to induce robust cytotoxic effects towards human leukemic lymphoblasts as single agents. In addition, others have shown that aberrant NOTCH-1 can antagonize glucocorticoid-induced cell death in normal developing thymocytes. Still further, severe gastrointestinal toxicity limits the clinical application of GSIs. Accordingly, a need exists for methods and compositions that enhance the efficacy of, mitigate resistance to, and reduce the gut toxicity of GSIs in the treatment of T-ALL and other conditions, such as Alzheimer's disease.

SUMMARY OF THE INVENTION

According to a first preferred embodiment of the present invention, methods are provided for treating or ameliorating the effects of a condition in a patient, which comprises administering to a patient an effective amount of a NOTCH-1 inhibitor (or an inhibitor of Aβ peptide production) and a glucocorticoid.

Another embodiment of the invention is a method for treating or ameliorating the effects of a condition in a patient characterized by resistance to glucocorticoid therapy, which method comprises administering to the patient an effective amount of a NOTCH-1 inhibitor (or an inhibitor of Aβ peptide production) and a glucocorticoid.

In other embodiments of the present invention, methods are provided for (a) treating a patient with a lymphoid malignancy that is resistant to glucocorticoid therapy, (b) treating a patient having a disease selected from the group consisting of T-cell lymphoblastic leukemia (T-ALL) and lymphoma, which disease is characterized by activating mutations in a NOTCH-1 gene, (c) increasing the efficacy of a glucocorticoid in treating a patient having a disease selected from the group consisting of T-cell lymphoblastic leukemia (T-ALL) and lymphoma, (d) modulating BIM gene expression in a patient having a disease selected from the group consisting of T-cell lymphoblastic leukemia (T-ALL) and lymphoma, and (e) treating or ameliorating the effects of a relapsed form of T-cell lymphoblastic leukemia or lymphoma. Each of these methods comprise administering to a patient in need thereof an effective amount of a γ-secretase inhibitor (GSI) and a glucocorticoid.

According to certain related embodiments, methods are provided for (i) inducing apoptosis in glucocorticoid-resistant T-cell lymphoblastic leukemia (T-ALL) cells, (ii) modulating BIM gene expression in glucocorticoid-resistant T-cell lymphoblastic leukemia (T-ALL) cells, and (iii) reversing glucocorticoid resistance in T-cell lymphoblastic leukemia (T-ALL) cells that have activating mutations in NOTCH-1. Such methods comprise contacting the cells with an effective amount of a γ-secretase inhibitor and a glucocorticoid.

According to further embodiments of the invention, compositions are provided that comprise a combination of one or more NOTCH-1 inhibitors (or one or more inhibitors of Aβ peptide production), one or more glucocorticoids, and, optionally, a pharmaceutically acceptable carrier. Such compositions are useful, for example, in preventing, treating, or ameliorating the effects of T-cell lymphoblastic leukemia, lymphoma, other cancers, and/or Alzheimer's disease.

According to certain related embodiments, compositions are provided for treating or ameliorating the effects of a disease selected from the group consisting of T-cell lymphoblastic leukemia (T-ALL) and lymphoma. Such compositions comprise a γ-secretase inhibitor (GSI), a glucocorticoid, and a pharmaceutically acceptable carrier.

According to still further embodiments of the invention, kits are provided for treating or ameliorating the effects of T-cell lymphoblastic leukemia, lymphoma, and/or other cancers. Such kits comprise, in packaged combination, a γ-secretase inhibitor, one or more glucocorticoids, and instructions for use.

According to certain additional embodiments of the invention, methods are provided for (a) preventing, treating, or ameliorating a side-effect of a NOTCH-1 inhibitor (or an inhibitor of Aβ peptide production) in a patient and (b) reversing, in a patient, secretory intestinal metaplasia, which is induced by GSI therapy, wherein such methods comprise administering to the patient an effective amount of a glucocorticoid.

According to still further embodiments of the invention, methods are provided for (a) preventing, treating, or ameliorating the effects of a condition in a patient characterized by increased production of amyloidogenic Aβ peptides in the patient's cerebral cortex and (b) preventing, treating, or ameliorating the effects of Alzheimer's disease, which methods comprise administering to the patient an effective amount of a NOTCH-1 inhibitor (or an inhibitor of Aβ peptide production) and a glucocorticoid.

According to yet further embodiments of the invention, compositions are provided for (a) preventing, treating, or ameliorating a side-effect of a NOTCH-1 inhibitor (or an inhibitor of Aβ peptide production) in a patient and (b) preventing, treating, or ameliorating the effects of intestinal secretory metaplasia caused by γ-secretase inhibitor (GSI) therapy in a patient. Such compositions comprise a NOTCH-1 inhibitor (or an inhibitor of Aβ peptide production), a glucocorticoid, and a pharmaceutically acceptable carrier.

According to still further embodiments of the invention, kits are provided for (a) preventing, treating, or ameliorating the effects of a condition in a patient characterized by increased production of amyloidogenic Aβ peptides in the patient's cerebral cortex and (b) treating a patient in need of γ-secretase inhibitor (GSI) therapy. Such kits generally comprise, in packaged combination, a γ-secretase inhibitor (GSI), a glucocorticoid and instructions for their use.

BRIEF DESCRIPTION OF THE FIGURES

The file of this patent or patent application contains at least one drawing executed in color. Copies of this patent or patent application with color drawing(s) will be provided by the United States Patent and Trademark Office upon request and payment of the necessary fee.

Figure 3:
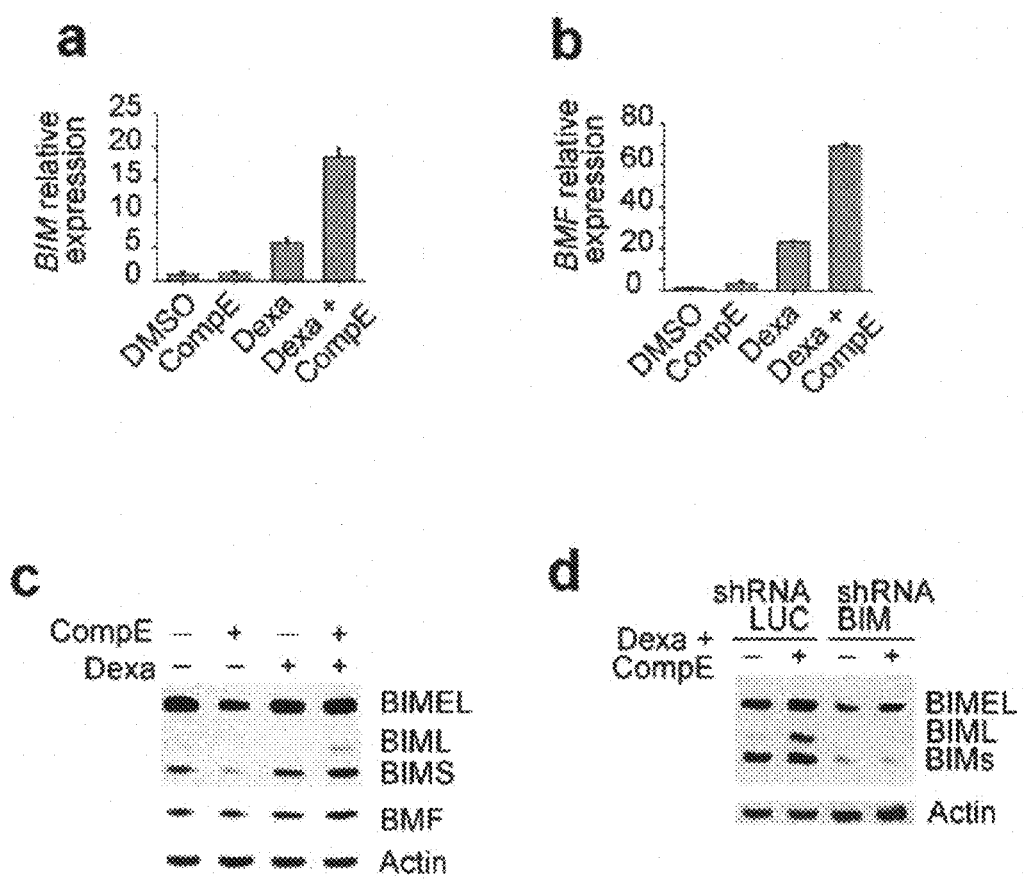

FIG. 3. BIM upregulation reverses glucocorticoid resistance in T-ALL cells treated with dexamethasone plus CompE. (a, b). Quantitative RT-PCR analysis of the BH3-only factors BIM (a) and BMF (b) in CUTLL1 cells treated with dexamethasone and/or CompE compared with vehicle only (DMSO). Relative expression levels are shown normalized to those of vehicle-only controls. (c). Western blot analysis of BIM and BMF in CUTLL1 cells treated with dexamethasone and/or CompE compared with vehicle only (DMSO). (d) Western blot analysis of BIM by sRNA knock down. CUTLL1 cells infected with control lentivirus targeting the luciferase gene (pLKO LUC) or BIM (pLKO BIM) were treated with vehicle only or dexamethasone plus CompE for 24 hours and analyzed by Western blotting. (e) Induction of apoptosis in control (pLKO LUC infected) and BIM knock-down (pLKO BIM infected) cells treated with dexamethasone plus CompE. (f) Western blot analysis of BMF by sRNA knock down. CUTLL1 cells infected with control lentivirus targeting the luciferase gene (pLKO LUC) or BMF (pLKO BMF) were treated with vehicle only or dexamethasone plus CompE for 24 hours and analyzed by Western blot. (g) Induction of apoptosis in control (pLKO LUC infected) and BMF knock-down (pLKO BMF-infected) cells treated with dexamethasone plus CompE. Apoptosis refers to the percentage of annexinV positive/PI negative cells.

Figure 4:
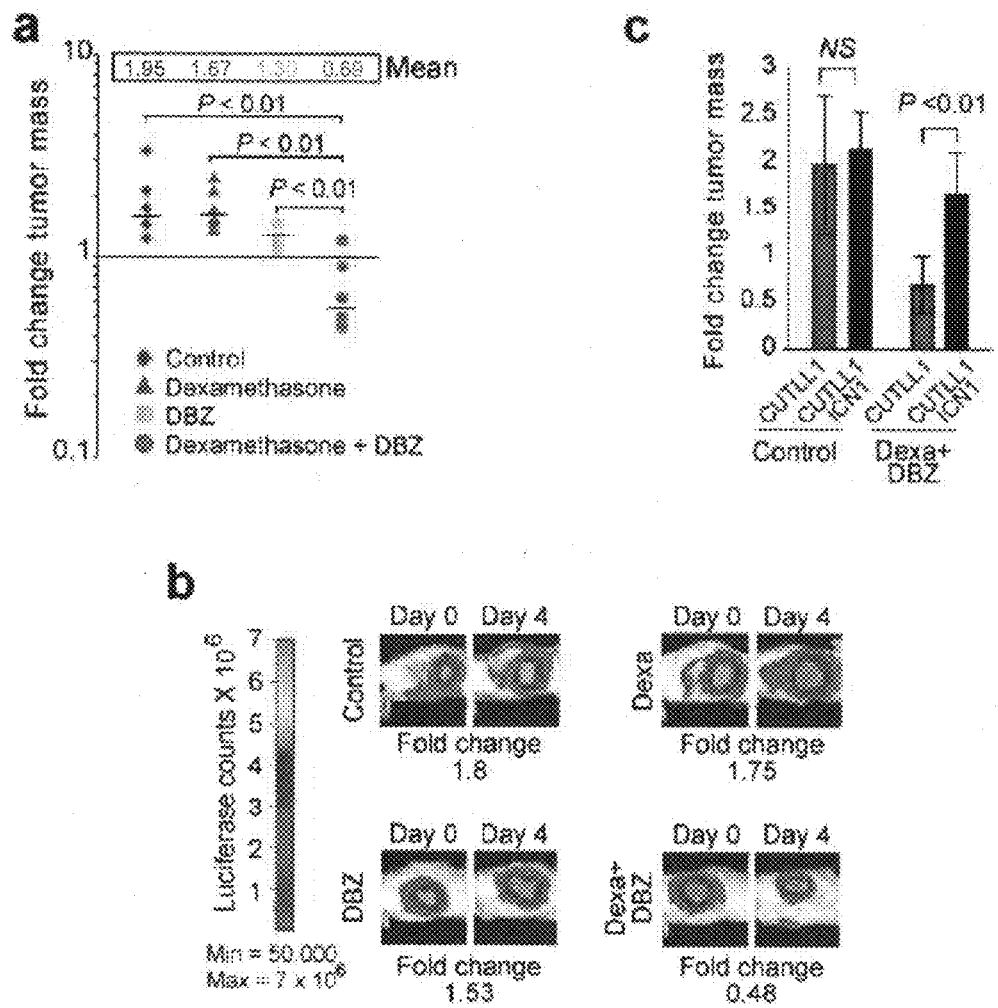

FIG. 4. DBZ reverses glucocorticoid resistance in vivo. (a) Tumor mass changes in subcutaneous CUTLL1 T-ALL xenografts in mice treated with vehicle (control), dexamethasone, GSI (DBZ) or GSI plus dexamethasone (Dexamethasone+DBZ) for 4 days as determined by bioimaging quantitation of tumor burden. (b) Representative examples of bioluminiscence in vivo imaging showing changes in tumor load in representative mice (animals with closest values to the median are shown) treated with vehicle (control), dexamethasone, DBZ and dexamethasone plus DBZ. (c) Tumor mass changes induced by dexamethasone plus DBZ treatment compared to controls in CUTLL1 T-ALL xenografts (CUTLL1) and CUTLL1 xenografts expressing an intracellular form of NOTCH1 (CUTLL1 ICN1), which does not require γ-secretase cleavage for activation. (d) Kaplan-Meier plot of overall survival among mice treated with vehicle (control), dexamethasone, DBZ or DBZ plus dexamethasone after xenograft transplantation of human T-ALL cells via tail vein injection. All deaths in the control and dexamethasone treatment groups were associated with tumor progression. Mice euthanized at the end of the observation period in the DBZ plus dexamethasone group were in complete remission. The abrupt drop in survival in the DBZ-treated group on day 20 was associated with severe intestinal toxicity. Two mice were euthanized on day 23 in the DBZ plus dexamethasone treated group because of excessive (>20%) weight loss.

Figure 5:
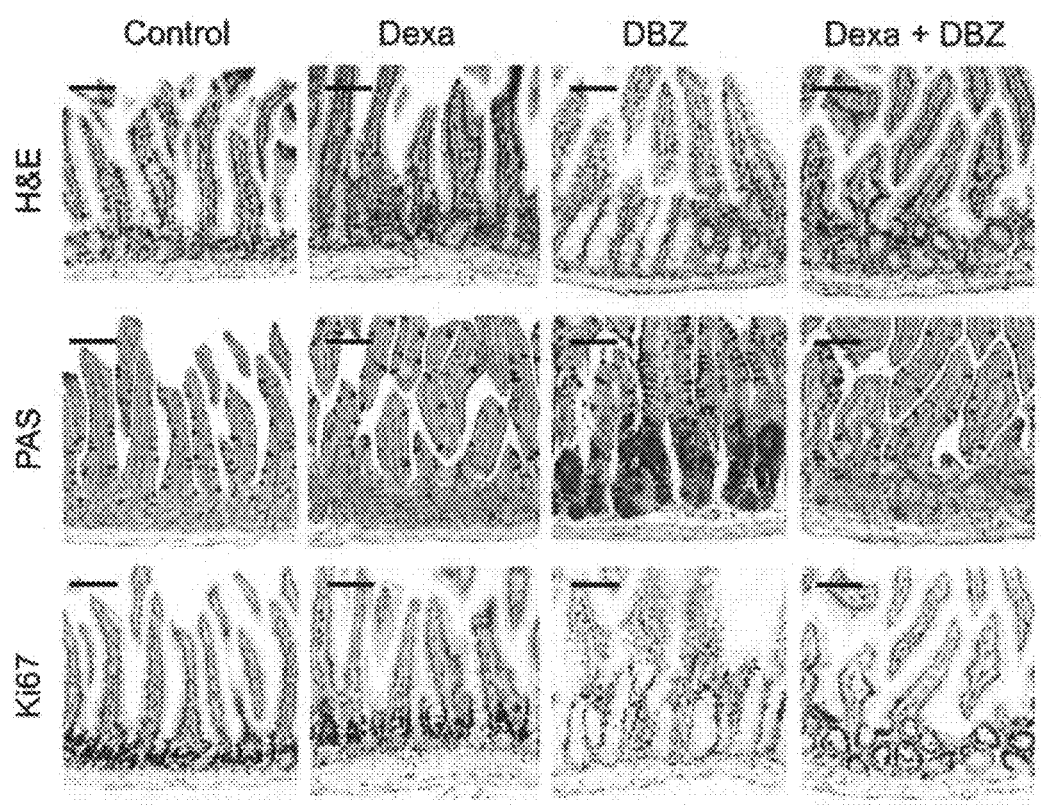

FIG. 5. Dexamethasone reverses GSI-induced gut toxicity in mice. Immunohistochemical studies of small intestines from control, dexamethasone-, DBZ- and dexamethasone plus DBZ-treated mice. As shown by haemotoxylin and eosin (H&E) and PAS staining, DBZ treatment (but not dexamethasone or DBZ plus dexamethasone treatment) resulted in conversion of the transit-amplifying crypt cell population to goblet cells. Ki67 staining showed similar proliferation rates for control-, dexamethasone- and dexamethasone plus DBZ-treated animals, whereas DBZ-treated mice showed a marked reduction in proliferation. Scale bars represent 100 µm.

Figure 6:
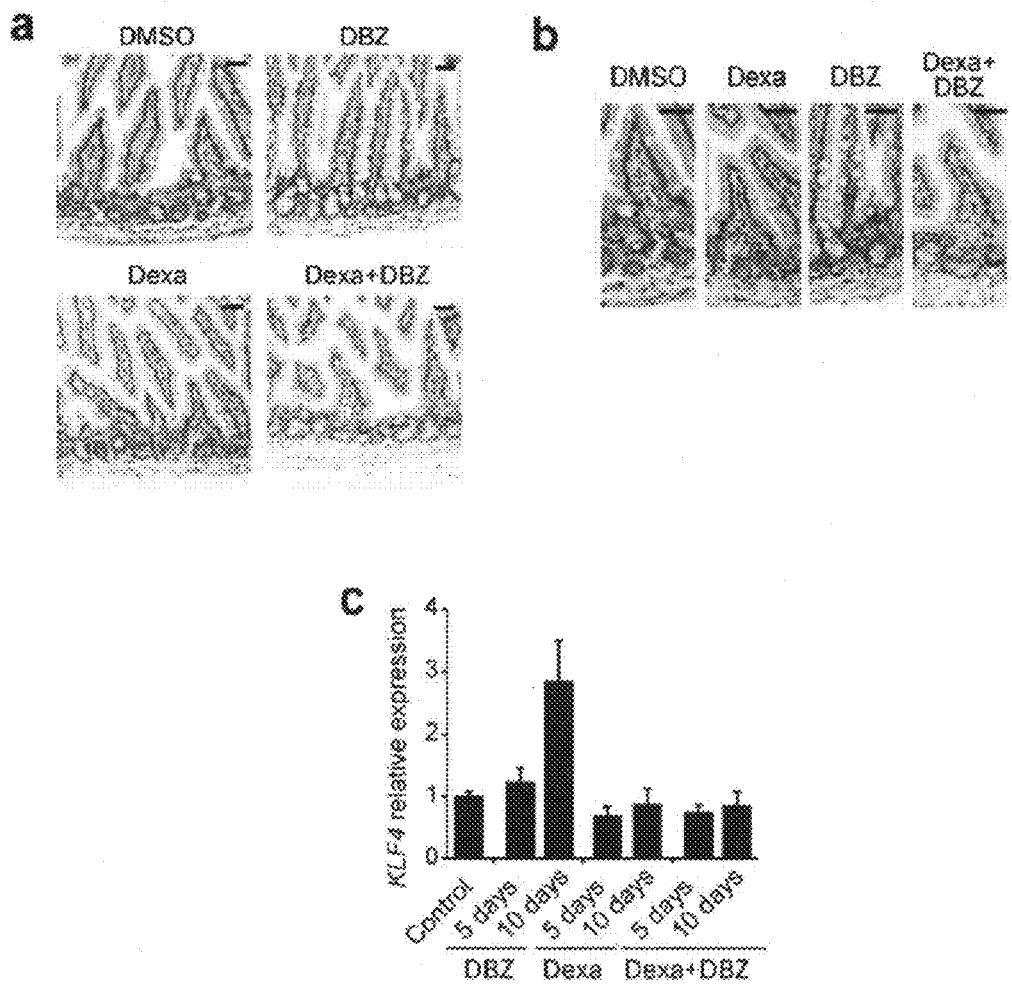

FIG. 6. KLF4 regulation by NOTCH signaling in the gut. (a,b) Immunohistochemistry analysis of Klf4 expression in small intestine of mice treated with dexamethasone, DBZ or the combination of dexamethasone plus DBZ for 5 days. Scale bars represent 100 µm. (c) Real-time PCR analysis of Klf4 transcript levels in small intestine of mice treated with dexamethasone, DBZ or the combination of dexamethasone plus DBZ for 5 and 10 days. Gapdh levels were used as a reference control. Data are means±s.d. of three animals per group. (d) Effects of ICN1 and HES1 expression in human KLF4 promoter activity. Luciferase reporter assays were performed in AGS cells with a 2,006 base pair (bp) Klf4 promoter construct (pGL2 KLF4p). Promoter activity is shown relative to an internal control expressing Renilla luciferase. (e) Quantitative ChIP analysis of HES1 binding to KLF4 promoter sequences. TIS: transcription initiation site. (f) Lentiviral shRNA knock-down of HES1 in HT29 cells induces transcriptional upregulation of KLF4. Expression of a control shRNA targeting the luciferase gene (shRNA LUC) was used as control. Data in (d-f) are means±s.d. of triplicate experiments.

Figure 7:
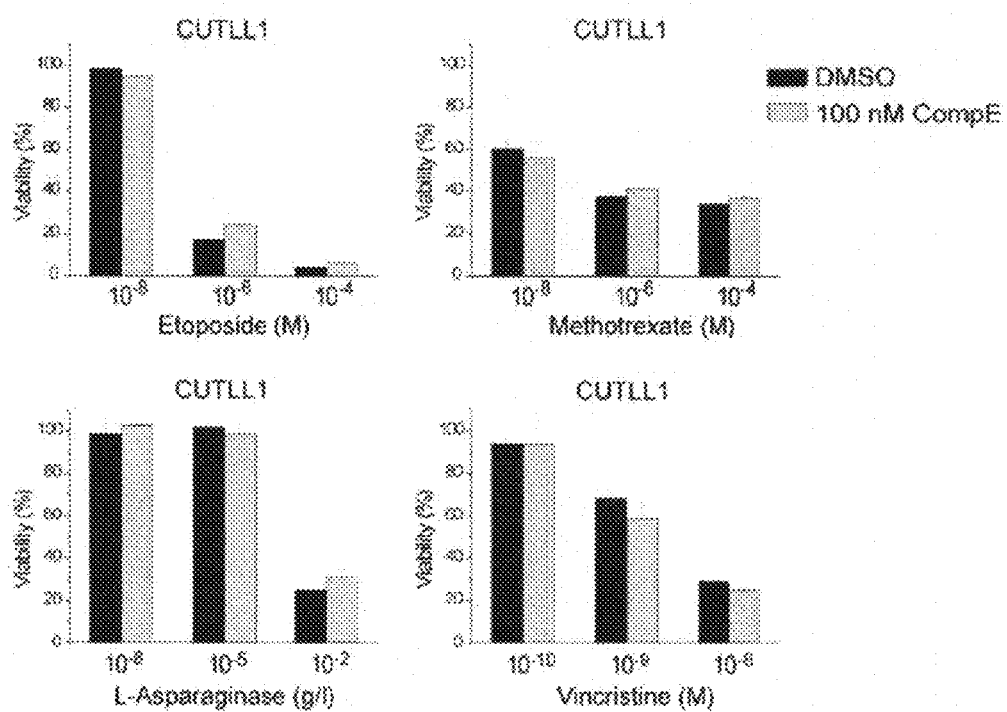

FIG. 7. Analysis of the effects of GSI treatment in chemotherapy response. Cell viability analysis in the CUTLL1 cells treated with 100 nM CompE or vehicle only in presence of increasing concentrations of etoposide, methotrexate, L-asparaginase and vincristine. Cell viability was analyzed by an MTT assay and cytotoxicity data was represented as percentage of viable cells compared with non-treated controls. Data are means±s.d. of triplicate experiments.

Figure 8:
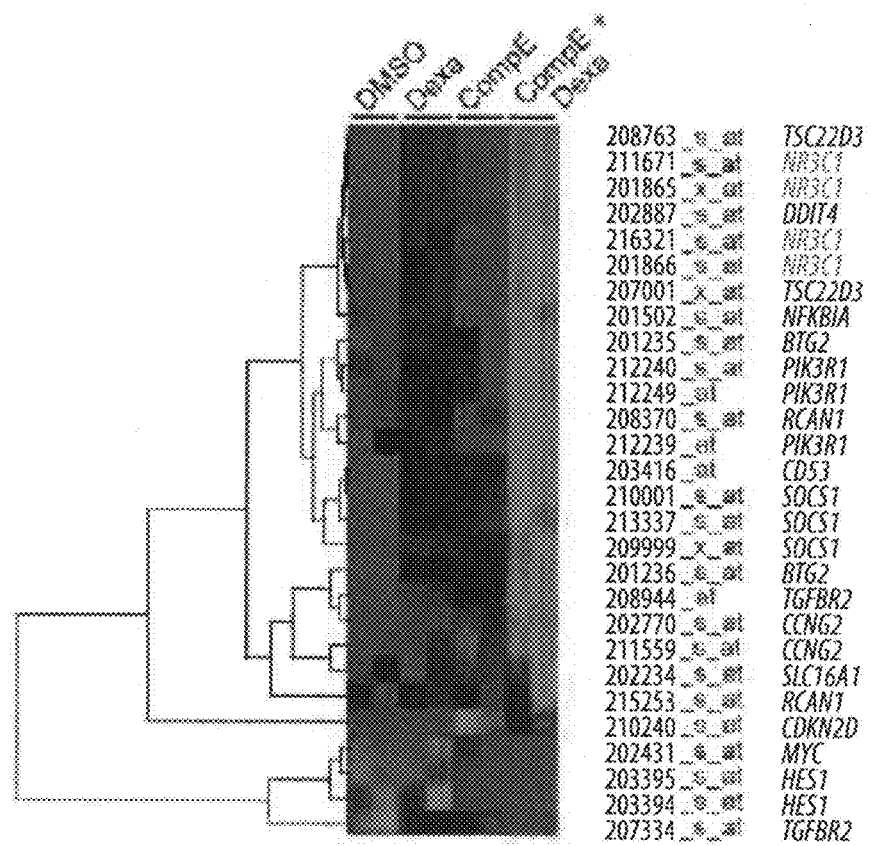

FIG. 8. Expression changes induced by dexamethasone plus CompE cotreatment in glucocorticoid regulated genes. The heat map on the left shows relative expression levels in CUTLL1 cells treated with DMSO, dexamethasone, CompE and Dexamethasone plus CompE for the most consistent glucocorticoid regulated transcripts identified across multiple microarray studies. Expression levels are color coded with red (darker grey) indicating higher levels of expression and green (lighter grey) indicating lower levels of expression. Genes are displayed as organized by hierarchical clustering using Cluster and Treeview. Venn diagrams on the right show the overlap between genes regulated by dexamethasone treatment and genes differentially upregulated (a, b, c) or downregulated (d, e) by CompE plus dexamethasone cotreatment versus DMSO, CompE or dexamethasone treatment alone. The number of genes in each category and the criteria used for selection of GSI plus glucocorticoid differential regulation versus DMSO, CompE or dexamethasone treatment alone are indicated. The significance of overlap between dexamethasone regulated genes and those showing differential regulation by dexamethasone plus CompE was tested by Fisher's exact test. These results indicate a broad synergistic effect of dexamethasone plus CompE in CUTLL1 cells with increased upregulation or downregulation of glucocorticoid regulated transcripts.

Figure 9:
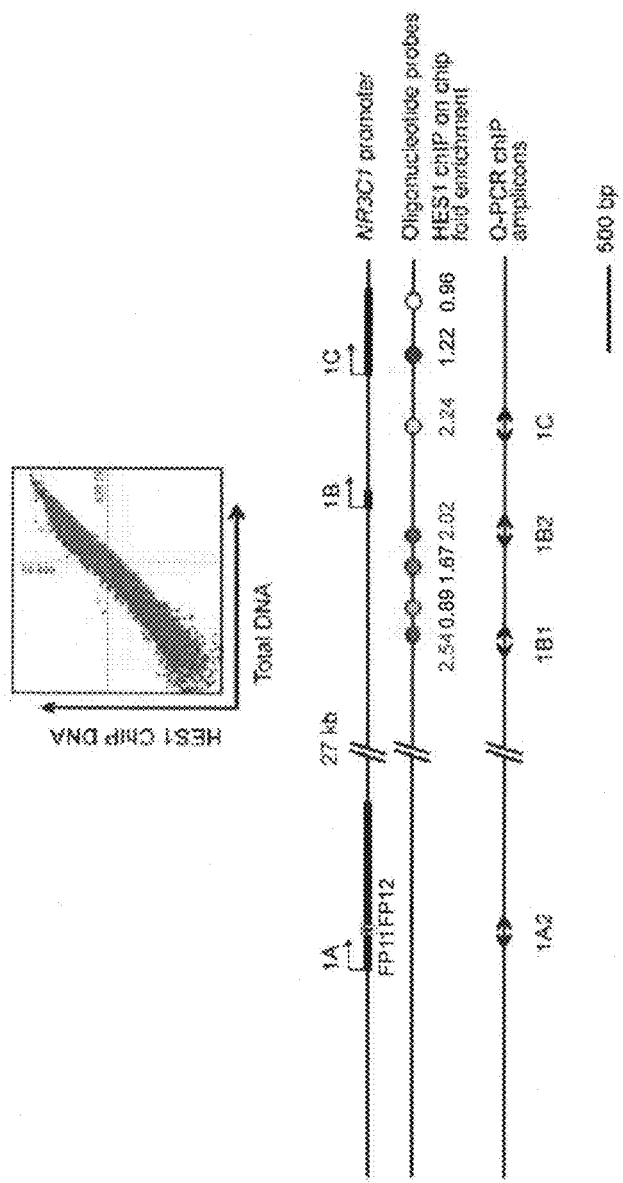

FIG. 9. ChIP-on-chip analysis of HES1 binding to the glucocorticoid receptor locus. The scatter plot on the top shows data from HES1 chIP-on-chip analysis using the Agilent 44K promoter array. The logarithm of fluorescence intensities of HES1 immunoprecipitated chromatin fragments from the HPB-ALL T-ALL cell line in the Y axis plotted against those of total chromatin in the X axis. The diagram at the bottom shows: (i) the structure of the glucocorticoid receptor promoters 1A, 1B and 1C, which are responsible glucocorticoid receptor autoregulation; (ii) the position of each of the seven oligonucleotide probes at the glucocorticoid receptor locus in the Agilent 44K promoter array with their corresponding chiP-on-chip enrichment values calculated with Agilent Gene Analitics software; and (iii) the position of PCR amplicons used to analyze the enrichment of glucocorticoid receptor promoters 1A, 1B and 1C in HES1 chromatin immunoprecipitates by Q-PCR in the CUTLL1 T-ALL cell line. FP11 (fingerprint 11) and FP12 (fingerprint 12) are regulatory sequences critically involved in glucocorticoid receptor promoter 1A autoregulation.

Figure 10:
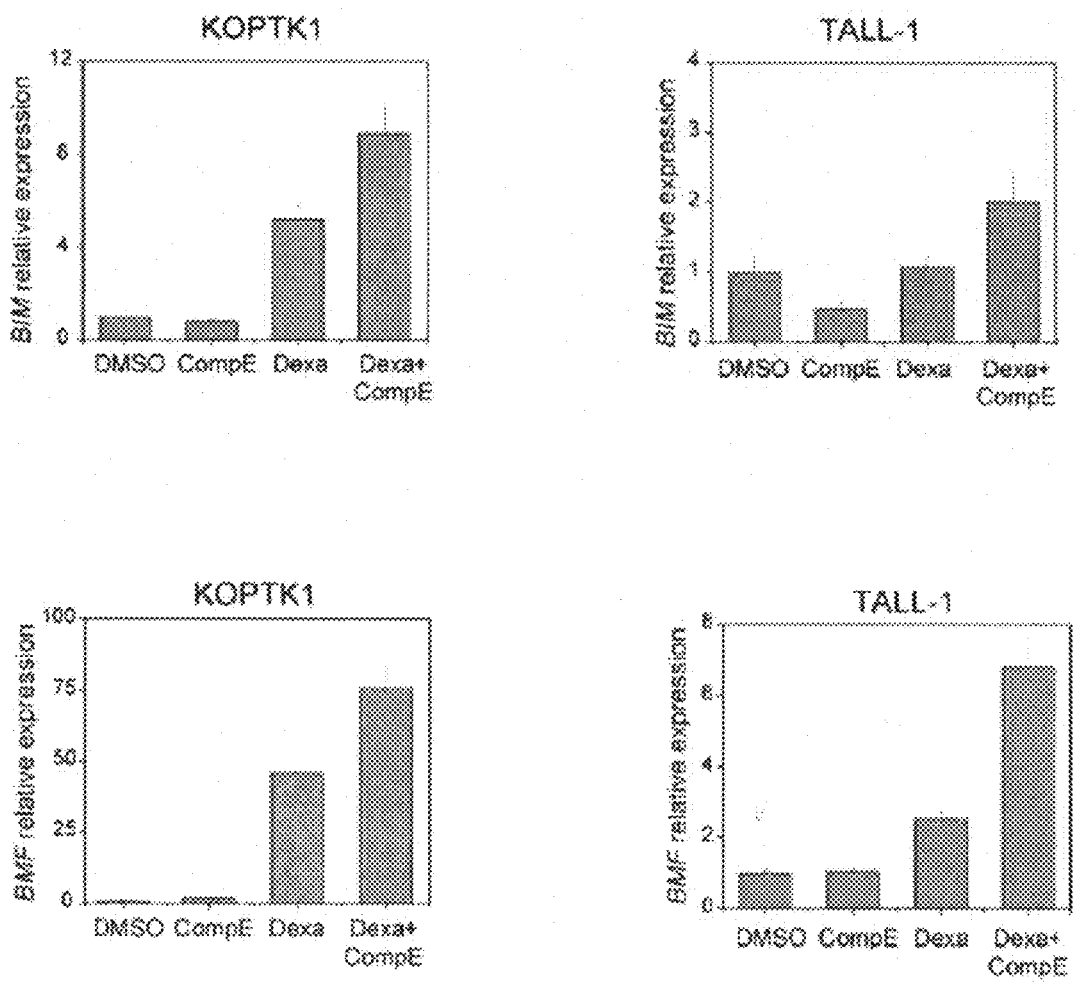

FIG. 10. Gene expression analysis of BIM and BMF in glucocorticoid-resistant T-ALL cells. Quantitative RT-PCR analysis of BIM and BMF in additional glucocorticoid-resistant T-ALL cells (KOPTK1 and TALL1) showing reversal of glucocorticoid resistance upon treatment with CompE plus dexamethasone. Relative expression levels are shown normalized to those of vehicle only treatment controls. Data are means±s.d. of triplicate experiments.

Figure 11:
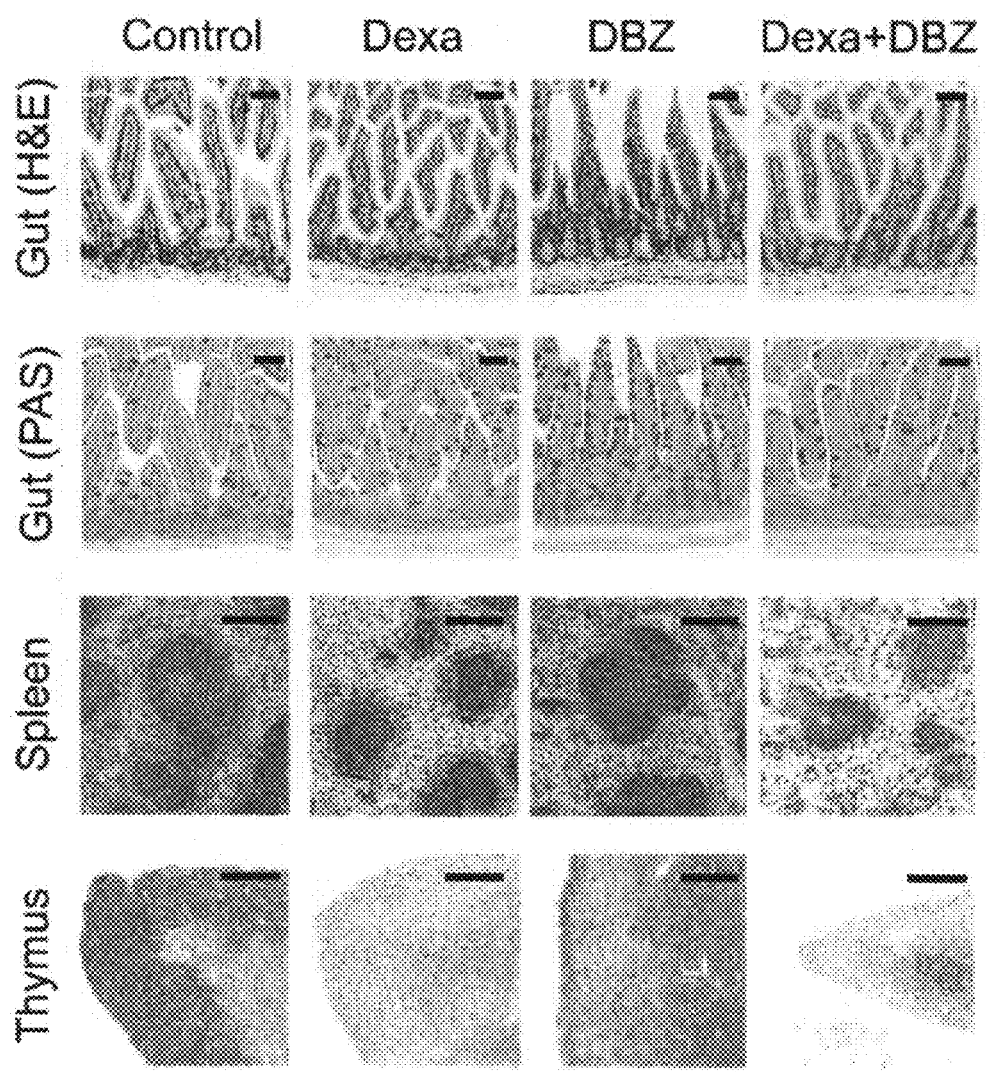

FIG. 11. Histopathology of the gut, spleen and thymus after 5 days of dexamethasone and/or GSI treatment with DBZ. Histological analysis of the small intestine of mice treated for 5 days with dexamethasone (Dexa), a GSI (DBZ), dexamethasone plus GSI (Dexa+DBZ) or vehicle only (control) stained with hematoxilin eosine (H&E) shows moderate secretory metaplasia with increased number of goblet cells in animals treated with DBZ. Increased goblet cell numbers are more evident in PAS staining. Dexamethasone and dexamethasone plus GSI showed no histopathological changes in the gut. Spleens from dexamethasone treated animals showed moderate disorganization of the red pulp and atrophy of the white pulp with preservation of the marginal zone. DBZ treated animals showed loss of the marginal zone of the spleen. DBZ plus dexamethasone treated mice showed increased disorganization of the red pulp, disappearance of the marginal zone and marked atrophy of the white pulp. Both dexamethasone and DBZ treatment induced thymic atrophy with loss of the lymphoid cells from the cortex which was more severe in animals treated with dexamethasone plus DBZ in combination. Scale bars represent 100 μm.

Figure 12:
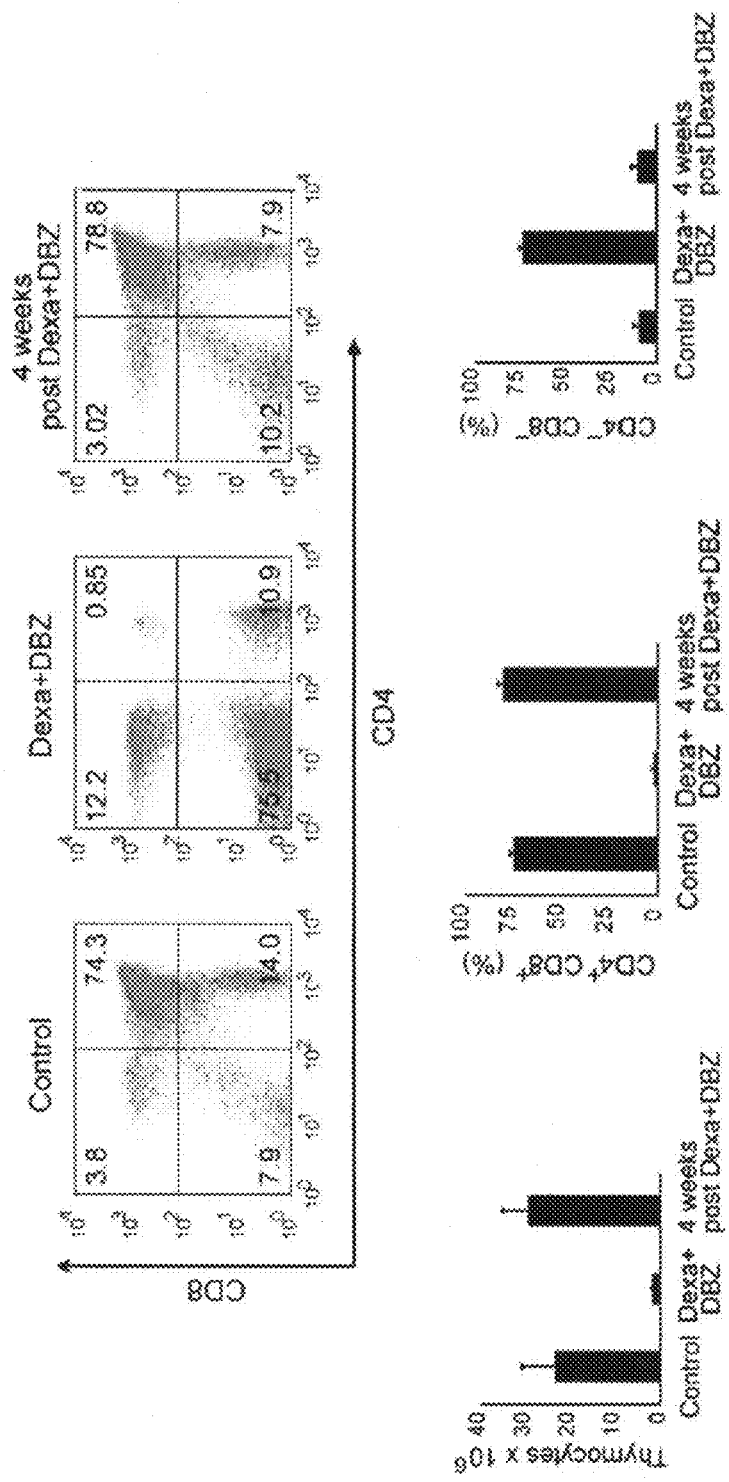

FIG. 12. Reversibility of the effects of dexamethasone plus DBZ in the thymus. Flow cytometry analysis of thymocyte populations in animals treated with DMSO (Control) and dexamethasone plus DBZ immediately after 5 days of treatment (Dexa+DBZ); or after 4 weeks off therapy following 5 days of treatment with dexamethasone plus DBZ (4 weeks post Dexa+DBZ). Treatment with dexamethasone plus DBZ for 5 days induced a marked reduction in the cellularity of the thymus and a marked depletion of double positive thymocytes. However, these effects were transient as demonstrated by reconstitution of total thymocyte cell numbers and double positive cells in animals analyzed 4 weeks after the last dose of dexamethasone plus DBZ treatment. Bar diagrams show means±s.d. of triplicate experiments.

Figure 13:
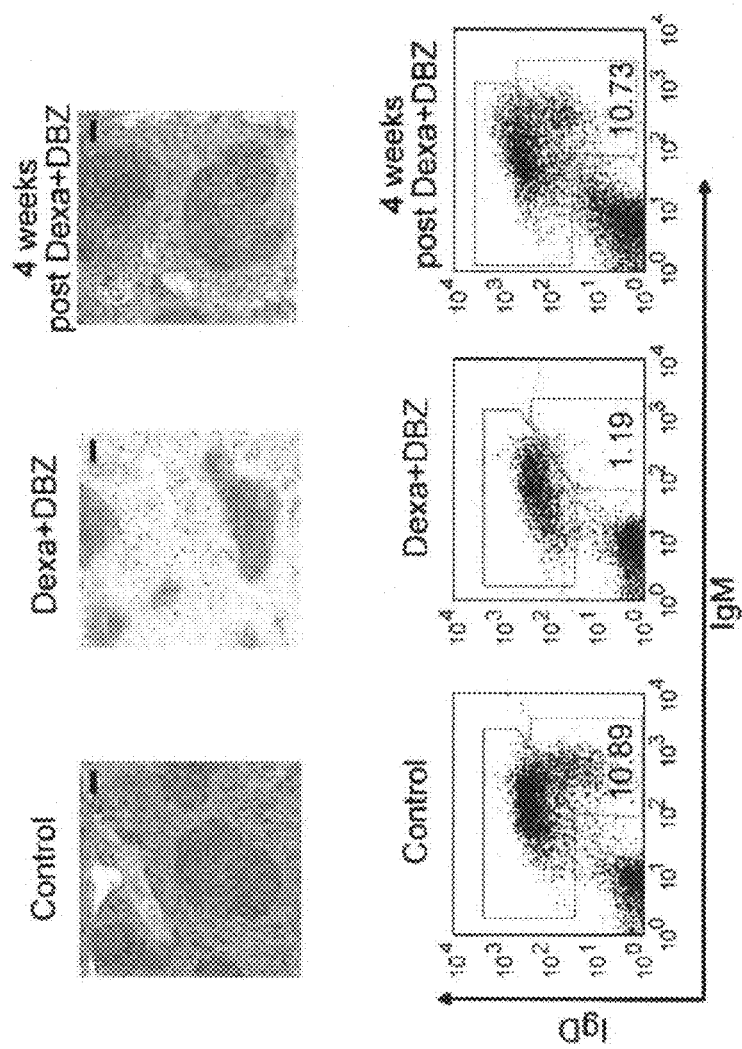

FIG. 13. Reversibility of the effects of dexamethasone plus DBZ in the spleen. Histological and flow cytometry analysis of the spleen in animals treated with DMSO (Control) and dexamethasone plus. DBZ immediately after 5 days of treatment (Dexa+DBZ); or after 4 weeks off therapy following 5 days of treatment with dexamethasone plus DBZ (4 weeks post Dexa+DBZ). Treatment with dexamethasone plus DBZ for 5 days induced a marked reduction in the cellularity of the spleen with disorganization of the red pulp, atrophy of the lymphoid follicles and ablation of the marginal zone B cells ($IgM^+IgD^-$ population). Analysis of animals 4 weeks after the last dose of dexamethasone plus DBZ demonstrated that the effects of GSI plus glucocorticoid treatment in the spleen are reversible with restoration of the cellularity and architecture of the organ and repopulation of the marginal zone B-cell compartment. Bar diagrams show means±s.d. of triplicate experiments.

Figure 14:
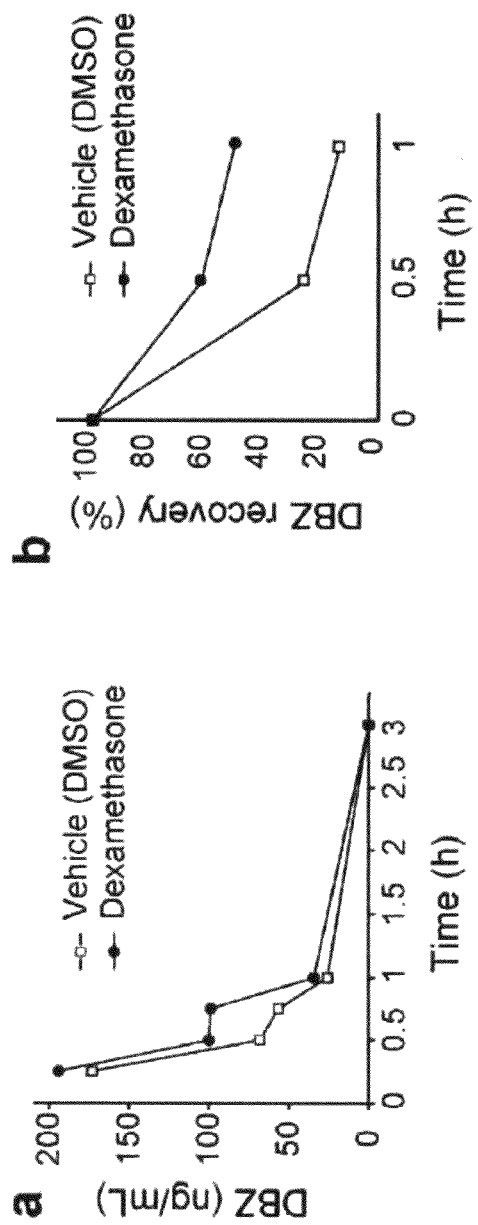

FIG. 14. Effects of dexamethasone in DBZ metabolism in vivo and in vitro. (a) Pharmacokinetic analysis of DBZ in animals treated with dexamethasone or vehicle only (DMSO) for 5 days. (b) Analysis of DBZ metabolism by liver microsomes in vitro showing decreased the metabolization of DBZ in the presence of dexamethasone compared to vehicle controls (DMSO).

DETAILED DESCRIPTION OF THE INVENTION

According to a first preferred embodiment of the present invention, methods are provided for preventing, treating, and/or ameliorating the effects of a condition, such as a condition that is characterized by resistance to glucocorticoid therapy, in a patient. Such embodiments generally include administering to the patient an effective amount of a NOTCH-1 inhibitor (or an inhibitor of Aβ peptide production) and a glucocorticoid.

In these embodiments, the condition includes any disease that may be prevented, treated, or its effects ameliorated by administering a NOTCH-1 inhibitor (or an inhibitor of Aβ peptide production) and a glucocorticoid to a patient suffering from the condition. In the present invention, the condition may be cancer or a neurodegenerative disease, such as Alzheimer's disease or Huntington's disease. Preferably, the cancer is a lymphoid malignancy that is resistant to glucocorticoid therapy, such as for example, T-cell lymphoblastic leukemia (T-ALL) or lymphoma, which is characterized by activating mutations in a NOTCH-1 gene.

As used herein, "T-ALL or lymphoma, which is characterized by activating mutations in a NOTCH-1 gene" means that T-ALL or lymphoma cells in a patient's body harbor one or more mutations in a NOTCH-1 gene. Typically, such mutations render such a patient resistant to glucocorticoid therapy.

Whether a patient harbors an activating NOTCH-1 mutation may, optionally, be determined prior to the provision of the glucocorticoid and NOTCH-1 inhibitor, e.g., GSI combination. The presence or absence of a NOTCH-1 mutation may be determined using standard procedures, such as determining whether a patient harbors a nucleic acid sequence that encodes a mutated form of the NOTCH-1 receptor. In the event that a mutated form of NOTCH-1 is detected in a patient, the glucocorticoid and NOTCH-1 inhibitors may be provided to such patient, particularly if such patient is suffering from a lymphoid malignancy, such as for example, T-cell lymphoblastic leukemia, lymphoma, and/or other cancers.

In the present invention, any known or to-be-discovered glucocorticoid may be used, so long as it provides a synergistic effect when administered with a NOTCH-1 inhibitor, GSI inhibitor, or an inhibitor of Aβ peptide production. Non-limiting examples of glucocorticoids that may be used in the present invention include cortisol, budesonide, hydrocortisone, dexamethasone, prednisone, prednisolone, and methylprednisolone. The present invention includes any form of the glucocorticoid, including pro-drug forms, as well as precursors, analogs, enantiomers, optical isomers, diastereomers, N-oxides, crystalline forms, hydrates, metabolites or pharmaceutically acceptable salts thereof. These glucocorticoids may be used alone (i.e., a single glucocorticoid with a NOTCH-1 inhibitor, GSI inhibitor, or an inhibitor of Aβ peptide production) or in any combination.

In the present invention, any known or to-be-discovered NOTCH-1 inhibitor (or inhibitor of Aβ peptide production) may be used, so long as it provides a synergistic effect when administered with a glucocorticoid. In the present invention, a "NOTCH-1 inhibitor" decreases the action of, and preferably substantially, if not completely, inhibits activation of the NOTCH-1 receptor. Preferably, the NOTCH-1 inhibitor is a GSI. Non-limiting examples of GSIs that may be used in accordance with the present invention include [(2S)-2-{[(3, 5-Difluorophenyl)acetyl]amino}-N-[(3S)]-methyl-2-oxo-5-phenyl-2,3-dihydro-1H-1,4-benzodiazepin-3-yl]propanamide] (CompE), N-[N-(3,5-difluorophenacetyl)-L-alanyl]-Sphenylglycine-t-butylester (DAPT) (Elan Pharmaceuticals, Dublin, Ireland), LY411575 (Elli Lily, Indianapolis, Ind.), (5S)-(t-Butoxycarbonylamino)-6-phenyl-(4R)hydroxy-(2R) benzylhexanoyl)-L-leu-L-phe-amide (L-685,458) (Merck, Whitehouse Station, N.J.), L-852,647 (Merck), MW167, WPE-III-31, LY450139, MRK003 (Merck), R-flurbiprofen ([1,1'-Biphenyl]-4-acetic acid, 2-fluoro-alpha-methyl), NGX-555 (TorreyPines Therapeutics), CZC-1040 (Cellzome, Johnson & Johnson, Inc.), E2012 (Eisai), GSM (Wyeth), Begacestat (2-Thiophenesulfonamide, 5-chloro-N-[(1S)-3,3,3-trifluoro-1-(hydroxymethyl)-2-(trifluoromethyl) propyl]-), GSI-SP (cyclic sulfonamides, Schering-Plough, NIC5-15 (Humanetics), BACE Inhibitor (Bristol-Myers Squibb), and CHF-5074 (Chiesi). The present invention includes any form of the NOTCH-1 inhibitor, GSI, or inhibitor of Aβ peptide production, including pro-drug forms, as well as precursors, analogs, enantiomers, optical isomers, diastereomers, N-oxides, crystalline forms, hydrates, metabolites or pharmaceutically acceptable salts thereof.

These NOTCH-1 inhibitors, GSIs, and/or inhibitors of Aβ peptide production may be used alone (e.g., a NOTCH-1 inhibitor and/or a GSI with a glucocorticoid) or in any combination. Thus, in the present invention, one or more glucocorticoids may be administered with one or more NOTCH-1 inhibitors, GSIs, and/or inhibitors of Aβ peptide production.

In these methods, preferably the NOTCH-1 inhibitor is CompE or a pharmaceutically acceptable salt thereof and the glucocorticoid is dexamethasone or a pharmaceutically acceptable salt thereof.

In other embodiments, methods are provided for (1) treating a patient with a lymphoid malignancy that is resistant to glucocorticoid therapy or (2) treating a patient that has T-cell lymphoblastic leukemia (T-All) and/or lymphoma, which diseases are characterized by activating mutations in a NOTCH-1 gene. In further embodiments, methods are provided for (3) increasing the efficacy of a glucocorticoid in treating a patient having T-cell lymphoblastic leukemia (T-ALL) and/or lymphoma, (4) modulating BIM gene expression in a patient having T-cell lymphoblastic leukemia (T-ALL) and/or lymphoma, or (5) treating or ameliorating the effects of a relapsed form of T-cell lymphoblastic leukemia (T-All) and/or lymphoma. In each of these embodiments, the method includes administering to the respective patients an effective amount of a GSI and a glucocorticoid as defined above. In each of these embodiments, it is preferred that the GSI is CompE or a pharmaceutically acceptable salt thereof and the glucocorticoid is dexamethasone or a pharmaceutically acceptable salt thereof.

The invention provides that the glucocorticoids and NOTCH-1 inhibitors, such as for example the GSIs, may be administered to the patient together (i.e., co-administered). Alternatively, the glucocorticoids and NOTCH-1 inhibitors, such as for example the GSIs, may be serially administered. For example, the glucocorticoid composition may be administered to the patient and, after a period of time, may be followed by the administration of at least one NOTCH-1 inhibitor, such as for example a GSI. Conversely, at least one NOTCH-1 inhibitor, such as for example a GSI, may be administered to the patient and, after a period of time, may be followed by the administration of a glucocorticoid composition.

The glucocorticoid:GSI ratio that is administered to the patient is not critical, so long as the desired clinical effect is achieved. Such a ratio may be determined empirically by a physician. For example, the GSI:glucocorticoid ratio may be from about 1:1 to about 1:99. Alternatively, the GSI:glucocorticoid ratio may be from about 99:1 to about 1:1.

According to certain related embodiments, methods are provided for (i) inducing apoptosis in glucocorticoid-resistant T-ALL cells, (ii) modulating BIM expression in glucocorticoid-resistant T-ALL cells, and (iii) reversing glucocorticoid-resistance in T-ALL cells. Such methods comprise contacting the cells, whether in vitro or in vivo, with an effective amount of a GSI and glucocorticoid as defined above. In each of these embodiments, it is preferred that the GSI is CompE or a pharmaceutically acceptable salt thereof and that the glucocorticoid is dexamethasone or a pharmaceutically acceptable salt thereof.

According to still further embodiments of the invention, compositions are provided that comprise a combination of one or more NOTCH-1 inhibitors (and/or one or more inhibitors of Aβ peptide production), one or more glucocorticoids, and, optionally, a pharmaceutically acceptable carrier. Such compositions are useful, for example, in preventing or ameliorating the effects of T-cell lymphoblastic leukemia, lymphoma, and/or other cancers and/or other diseases, such as for example, neurodegenerative diseases, such as Alzheimer's disease or Huntington's disease.

As referenced above, the clinical development of GSI-based therapies in T-ALL has been hampered by the limited ability of these drugs to induce apoptosis in human T-cell lymphoblasts by the development of severe gastrointestinal toxicity derived from inhibition of NOTCH signaling in the gut. Intestinal toxicity has also become a major obstacle in the development of GSI therapies aimed to block the production of amyloid Aβ peptides to slow down the progression of Alzheimer's disease.

Accordingly, the present invention further provides certain methods for (a) preventing, treating, or ameliorating a side-effect of a NOTCH-1 inhibitor (or an inhibitor of Aβ peptide production) in a patient and (b) reversing, in a patient, secretory intestinal metaplasia, which is induced by GSI therapy, wherein such methods comprise administering to the patient an effective amount of a glucocorticoid.

According to still further embodiments of the invention, methods are provided for (a) preventing, treating, or ameliorating the effects of a condition in a patient characterized by increased production of amyloidogenic Aβ peptides in the patient's cerebral cortex and (b) preventing, treating, or ameliorating the effects of Alzheimer's disease, which methods comprise administering to the patient an effective amount of a NOTCH-1 inhibitor (or an inhibitor of Aβ peptide production) and a glucocorticoid.

According to yet further embodiments of the invention, compositions are provided for (a) preventing, treating, or ameliorating a side-effect of a NOTCH-1 inhibitor (or an inhibitor of Aβ peptide production) in a patient and (b) preventing, treating, or ameliorating the effects of intestinal secretory metaplasia caused by γ-secretase inhibitor (GSI) therapy in a patient. Such compositions comprise a NOTCH-1 inhibitor (or an inhibitor of Aβ peptide production), a glucocorticoid, and a pharmaceutically acceptable carrier.

According to still further embodiments of the invention, kits are provided for (a) preventing, treating, or ameliorating the effects of a condition in a patient characterized by increased production of amyloidogenic Aβ peptides in the patient's cerebral cortex and (b) treating a patient in need of γ-secretase inhibitor (GSI) therapy. Such kits generally comprise, in packaged combination, a γ-secretase inhibitor (GSI), a glucocorticoid and instructions for their use.

In the present invention, an "effective amount" or "therapeutically effective amount" of a glucocorticoid, NOTCH-1 inhibitor (such as for example a GSI), and/or an inhibitor of Aβ peptide production is that amount of each that is sufficient to effect beneficial or desired results as described herein. In terms of treatment of a mammal, e.g., a human patient, an "effective amount" is an amount sufficient to (i) treat, prevent, manage, palliate, ameliorate, or stabilize a condition, such as a lymphoid malignancy, T-ALL, lymphoma, or other cancers amenable to treatment with a glucocorticoid and a NOTCH-1 inhibitor, such as for example a GSI, or (ii) substantially inhibit Aβ peptide production and/or mitigate the effects of Alzheimer's disease. Because both glucocorticoids, NOTCH-1 inhibitors, such as for example GSIs, and inhibitors of Aβ peptide production have been used separately in clinical situations, effective amounts for their use herein may be determined by a physician.

In the present invention, when a range is stated for a particular parameter, e.g., an effective amount, all values within that range, including the endpoints, are intended to be included. In addition to the foregoing, effective dosage forms, modes of administration, and dosage amounts of the glucocorticoid and NOTCH-1 inhibitor (or inhibitor of Aβ peptide production) may be determined empirically, and making such determinations is within the skill of the art in view of the disclosure herein. It is understood by those skilled in the art that the dosage amount will vary with the route of administration, the rate of excretion, the duration of the treatment, the identity of any other drugs being administered, the age, size, and species of mammal to be treated, and like factors well known in the arts of medicine and veterinary medicine. In general, a suitable dose of the glucocorticoid and NOTCH-1 inhibitor (or inhibitor of Aβ peptide production), e.g. GSI combination according to the invention will be that amount of such combination that is the lowest dose effective to produce the desired effect. The effective dose of the glucocorticoid and NOTCH-1 inhibitor (or inhibitor of Aβ peptide production), e.g. GSI combinations of the present invention may be administered as one, two, three, four, five, six or more sub-doses, administered separately at appropriate intervals throughout the day.

The glucocorticoid and NOTCH-1 inhibitor (or inhibitor of Aβ peptide production), e.g. GSI combinations of the present invention, may be administered in any desired and effective manner: as pharmaceutical compositions for oral ingestion, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. In the present invention, a preferred route of administration is intravenous. Further, the glucocorticoid and NOTCH-1 inhibitor (or inhibitor of Aβ peptide production), e.g. GSI combinations of the present invention, may be administered in conjunction with other treatments. The glucocorticoid and NOTCH-1 inhibitor (or inhibitor of Aβ peptide production), e.g. a GSI combination, or a composition containing such a combination, may be encapsulated or otherwise protected against gastric or other secretions, if desired.

While it is possible for the glucocorticoid and NOTCH-1 inhibitor (or inhibitor of Aβ peptide production), e.g. a GSI combination of the invention, to be administered alone, it is preferable to administer such combination as a pharmaceutical formulation (composition). Pharmaceutically acceptable compositions of the invention comprise one or more glucocorticoids, and one or more NOTCH-1 inhibitors (or one or more inhibitors of Aβ peptide production), as active ingredients in admixture with one or more pharmaceutically-acceptable carriers and, optionally, one or more other compounds, drugs, ingredients and/or materials. Regardless of the route of administration selected, the glucocorticoid and NOTCH-1 inhibitor (or inhibitor of Aβ peptide production), e.g. GSI combinations of the present invention may be formulated into pharmaceutically-acceptable dosage forms by conventional methods known to those of skill in the art. See, e.g., Remington's Pharmaceutical Sciences (Mack Publishing Co., Easton, Pa.).

Pharmaceutically acceptable carriers are well known in the art (see, e.g., Remington's Pharmaceutical Sciences (Mack Publishing Co., Easton, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups, and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active glucocorticoid and NOTCH-1 inhibitor, e.g. GSI combination. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active glucocorticoid and NOTCH-1 inhibitor, e.g. GSI combination may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise the glucocorticoid and NOTCH-1 inhibitor (or inhibitor of Aβ peptide production), e.g. a GSI combination, along with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, or solutes, which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug, it is desirable to slow its absorption from subcutaneous or intramuscular injection. In the present invention, it may be desirable to slow the absorbance of one, or more, or all of the actives. This may be accomplished by the use of a liquid suspension of crystalline or amorphous material having poor water solubility.

The rate of absorption of the drug(s) then depends upon its rate of dissolution which, in turn, may depend upon crystal size and crystalline form. Alternatively, delayed absorption of a parenterally-administered drug(s) may be accomplished by dissolving or suspending the drug in an oil vehicle. Injectable depot forms may be made by forming microencapsule matrices of the active ingredient(s) in biodegradable polymers. Depending on the ratio of the active ingredient(s) to polymer, and the nature of the particular polymer employed, the rate of active ingredient release can be controlled. Depot injectable formulations are also prepared by entrapping the drug(s) in liposomes or microemulsions which are compatible with body tissue. The injectable materials can be sterilized for example, by filtration through a bacterial-retaining filter.

The glucocorticoid and NOTCH-1 inhibitor (or inhibitor of Aβ peptide production), e.g. GSI combinations of the present invention, may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

According to still further embodiments of the invention, kits are provided for treating or ameliorating the effects of T-cell lymphoblastic leukemia, lymphoma, and/or other cancers. Such kits comprise, in packaged combination, a GSI, a glucocorticoid, and instructions for use. The GSI and glucocorticoid may be in unit dosage form, either stored separately or pre-mixed. The GSI and one or more glucocorticoids may further comprise a pharmaceutically acceptable carrier, as described above. Preferably, the GSI is CompE or a pharmaceutically acceptable salt thereof and the glucocorticoid is dexamethasone or a pharmaceutically acceptable salt thereof.

The following examples are provided to further illustrate the methods and compositions of the present invention. These examples are illustrative only and are not intended to limit the scope of the invention in any way.

EXAMPLES

Methods

Inhibitors and drugs. Both compound E (CompE) [(2S)-2-{[(3,5-difluorophenyl)-acetylamino}-N-[(3S)-1-methyl-2-oxo-5-phenyl-2,3-dihydro-1H-1,4-benzodiazepin-3-yl]propanamide] (Alexis Biochemicals, Lausen, Switzerland) and DBZ (2S)-2-[2-(3,5-difluorophenyl)-acetylamino]-N-(5-methyl-6-oxo-6,7-dihydro-5H-dibenzo[b,d]azepin-7-yl)-propionamide (SYNCOM BV, Groningen, the Netherlands) are cell permeable, selective, non-transition state and non-competitive inhibitors of γ-secretase. Z-VAD, dexamethasone, etoposide, methotrexate, vincristine and RU486 were obtained from Sigma-Aldrich and L-asparaginase from Roche.

Proliferation and cell size assays. Cell growth ratios were determined by a colorimetric assay using the Cell Proliferation Kit I (MU) (Roche) in cell lines treated with different antileukemic drugs in the presence or absence of CompE (100 nM). The range of concentrations used in these experiments was: dexamethasone ($10^{-10}$ to $10^4$ M), etoposide ($10^{-10}$ to $10^{-4}$ M), methotrexate ($10^{-10}$ to $10^{-4}$ M), L-Asparaginase ($10^{-8}$ to $10^{-2}$ g/l) and vincristine ($10^{-12}$ to $10^{-6}$ M).

Retroviral and lentiviral transduction of cDNA and shRNA constructs. MiGR and MiGR-ICN1 retroviral constructs expressing EGFP and ICN1 IRES GFP have been described before. A retroviral HES1 expressing construct (pMSCV puro HA-HES1) was generated by PCR amplification and cloning of an HA-tagged HES1 cDNA in the pMSCV puro vector. Retroviral particles were produced and used in spin infections. Hairpin oligonucleotide sequences targeting HES1 (target sequence: 5'-GACAGCATCTGAGCACAGA-3') (SEQ ID NO:1), BIM (target sequence: 5'-AAGGTAGACAATTGCAGCCTG-3') (SEQ ID NO:2), BMF (target sequence: 5'-GCCCAGAGTAAGGAATGTCTT-3') (SEQ ID NO:3) or the luciferase gene (target sequence 5'-CCTAAGGTTAAGTCGCCCTCG-3') (SEQ ID NO:4) were expressed from the pLKO-puro lentiviral vector. Lentivirus production and infections were performed as previously described. Lentiviral particles expressing a luciferase and neomycin phosphotransferase fusion transcript were generated with the FUW-Lucneo vector.

DNA microarray analysis. We extracted RNA from duplicate cultures of CUTLL1 cells treated for 24 hours with vehicle (DMSO), CompE (100 nM), dexamethasone (1 μM) and CompE (100 nM) plus dexamethasone (1 μM) and prepared samples for analysis with Affymetrix Human U133 Plus 2.0 arrays according to the manufacturer's instructions as previously described. Interarray intensity differences were normalized with Dchip and selected for analysis the 10,896 probes with least variation among experimental replicas. Genes with synergistic upregulation or downregulation upon CompE plus dexamethasone cotreatment were selected as those with increased or decreased levels of gene expression of at least 30% and 100 units over DMSO, CompE and Dexamethasone treatments. To establish the correlation of expression data with NR3C1 levels we performed Nearest-neighbor analysis using the signal-to-noise statistic (δ class 0-δ class 1)/(δ class 0-δ class 1).

Quantitative real-time PCR. Total RNA from T-ALL cell lines was extracted with RNAqueous kit (Ambion) following the manufacturer's instructions. Total RNA from mouse tissues was extracted using Trizol reagent (Invitrogen). cDNA was generated with the ThermoScript RT-PCR system (Invitrogen) and analyzed by quantitative real-time PCR using SYBR Green RT-PCR Core Reagents kit and the 7300 Real-Time PCR System (Applied Biosystems). Relative expression levels were normalized with GAPDH expression used as a reference control.

Luciferase reporter assays. KLF4-luciferase reporter assays were performed in AGS cells transfected with a construct (pGL2 KLF4p) containing a human KLF4 proximal promoter and plasmids driving expression of HA-tagged ICN1 (pCS2-ICN1-HA) or HES1 (pEP7-HA-HES1) together with the pRL-CMV Renilla-luciferase expression plasmid. Klf4 reporter activity and Renilla luciferase levels were analyzed 48 hours after transfection.

ChIP-on-chip and quantitative ChIP analysis. HES1 (H-140, Santa Cruz Biotechnology) immunoprecipitates and control genomic DNA of HPB-ALL cells were differentially labeled with Cy3 and Cy5 and hybridized to the Agilent Proximal Promoter Arrays following standard procedures as previously described. To analyze visualize the binding ratios for probes located in the NR3C1 1B proximal promoter we used the Chip Analytics 1.1 software (Agilent Technologies) and the UCSC Genome Browser. For the analysis of ChIP enrichment of NR3C1 1A, 1B and 1C promoter sequences in CUTLL1 cells and of KLF4 promoter sequences in HT29 cells, real-time PCR was performed using ACTB genomic sequence levels as loading control in control genomic DNA (used as reference), and in anti-HES1 (H-140, Santa Cruz Biotechnology) and IgG control chromatin immunoprecipitates.

Western blot analysis. Antibodies against glucocorticoid receptor (E-20, Santa Cruz Biotechnology), BIM (Cell Signaling Technologies); BMF (BD Bioscience) and α-actin (C-11, Santa Cruz Biotechnology) were used in immunoblot assays following manufacturer instructions.

Mice and animal procedures. All mice were kept in specific pathogen-free animal facilities at the Memorial-Sloan Kettering Cancer Center and Columbia University Medical Center. All animal procedures were performed in accordance with the guidelines of the Institutional Animal Care and Use Committee. Xenograft experiments were performed with 6- to 8-week-old NOD/SCID female mice (Taconic Farms) as recipients. Toxicity experiments were carried out in 6-week-old C57/Black6 female mice (Jackson Laboratory).

Subcutaneous xenograft model and in vivo imaging. Luminiscent CUTLL1 cells were generated by infection of the CUTLL1 cell line with FUW-luc lentiviruses followed by selection with neomycin (1 mg/ml); luciferase expression was verified in vitro with the Dual-Luciferase Reporter Assay kit (Promega). For subcutaneous xenograft experiments, $2.5 \times 10^6$ T-ALL cells embedded in matrigel (BD Biosciences) were injected in the flank. After 1 week, mice were segregated into treatment groups (6 animals per group) and treated daily with vehicle (DMSO), dexamethasone (15 mg/kg), DBZ (10 µmol/kg) or dexamethasone (15 mg/kg) plus DBZ (10 µmol/kg) by intraperitoneal injection. For imaging studies, mice were anesthetized by isoflurane inhalation and injected with D-luciferin at 50 mg/Kg (Xenogen) intraperitoneally. Photonic emission was imaged with the In Vivo Imaging System (IVIS, Xenogen) with a collection time of 1 minute. Tumor bioluminescence was quantified by integrating the photonic flux (photons per second) through a region encircling each tumor as determined by the LIVING IMAGES software package (Xenogen).

Leukemia xenograft model. Before intravenous xenograft transplantation, recipient animals were irradiated with a total x-ray dose of 300 cGy. Two million CUTLL1 cells expressing luciferase were injected via the tail vein. After a 3-week window for tumor engraftment, mice with homogeneous tumor burdens were segregated into treatment groups (8 animals per group) and treated daily with vehicle (DMSO), dexamethasone (15 mg/kg), DBZ (10 µmol/kg) or dexamethasone (15 mg/kg) plus DBZ (10 µmol/kg) by intraperitoneal injection for 14 days. Disease progression/response was evaluated weekly using bioimaging as described above by integrating the photonic flux (photons per second) through a region around each mouse. Animals were followed up for up to 10 weeks. At the end of the observation period, single cell suspensions from the spleen of surviving animals were analyzed for the presence of leukemic cells by flow cytometry after staining with human anti-CD45-FITC (BD Biosciences).

Mouse toxicity model. To analyze the effects of GSI cotreatment with dexamethasone in healthy (non-leukemia-bearing) mice, we treated C57/Bl6 female animals (3 mice per group) daily with vehicle (DMSO), dexamethasone (15 mg/kg), DBZ (10 µmol/kg) and dexamethasone (15 mg/kg) plus DBZ (10 µmol/kg) by intraperitoneal injection for 5 and 10 days. At the end of the treatment, animals were euthanized and tissues and organs were collected and processed for histologic and immunohistochemical analysis.

Immunohistochemistry. anti-Ki67 (Dako) and anti-KLF4-immunostaining was performed on formalin-fixed paraffin-embedded tissue sections after antigen retrieval by microwave heating in citrate buffer (pH 6.0) for anti-Ki67 and by Trilogy (Cell Marque) for anti-KLF4. After epitope recovery slides were incubated with an antibody (anti-Ki67 1:50 and anti-KLF4 1:500 dilution) overnight at room temperature before antigen detection with diaminobenzidine (DAB) using a Ventana automated staining platform (Ventana).

Pharmacokinetic and drug metabolism studies. To analyze the effects of dexamethasone treatment in DBZ metabolism in vivo, DBZ (2 µmol/kg) was injected via the tail vein in vehicle-only or dexamethasone (15 mg/kg for 5 days) pretreated mice and DBZ concentrations were analyzed in mouse plasma by LC/MS/MS mass spectrometry in a Sciex API4000 triple quadrupole at serial timepoints. The concentration of DBZ in mouse plasma was determined using a standard curve (analyte peak area vs. concentration) generated with calibration standard pools.

To analyze the effects of dexamethasone in the hepatic metabolism of DBZ, mouse liver microsomes (Xenotech) were incubated with DBZ or dexamethasone plus DBZ at 37° C. and DBZ concentrations were analyzed by LC/MS/MS mass spectrometry in samples taken at serial timepoints using a standard curve prepared in incubation buffer with heat inactivated liver microsomes.

Results

Figure 1:
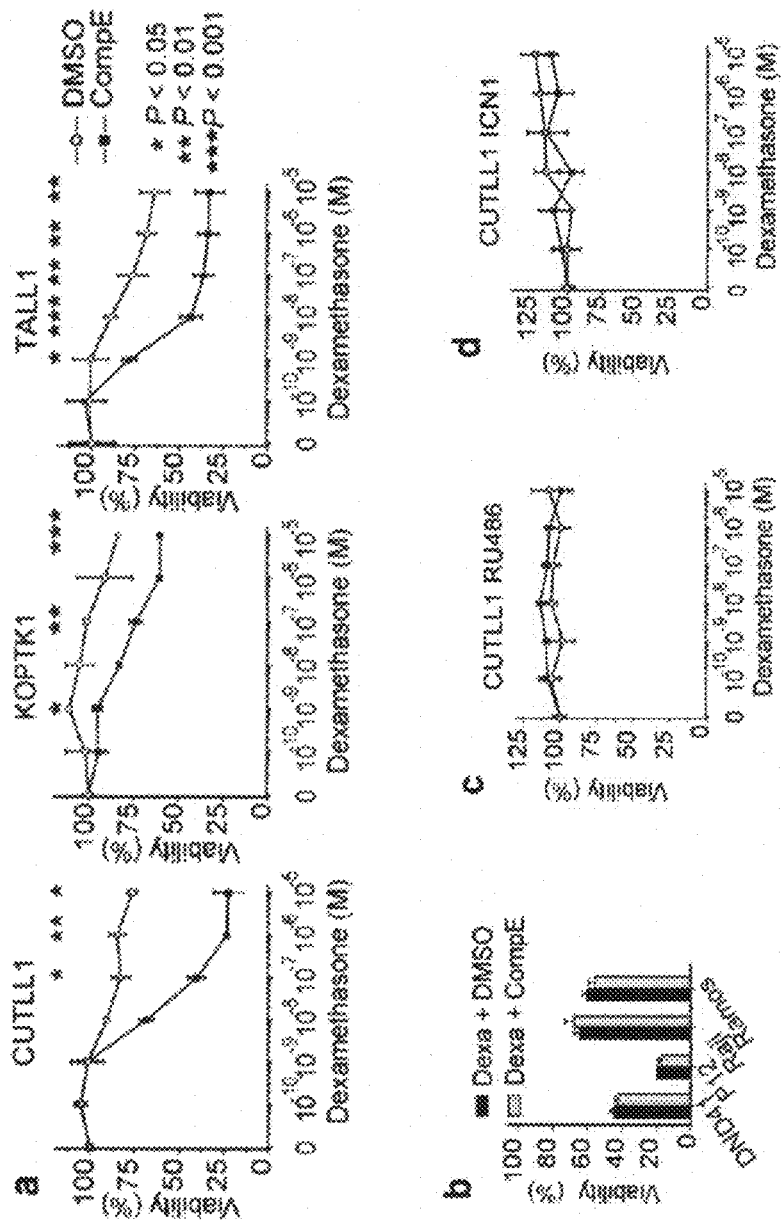
FIG. 1. GSIs reverse glucocorticoid resistance in T-ALL cells. (a-c). Viability assays in the glucocorticoid-resistant T-ALL cell lines CUTLL1 (72 hours), KOPTK1 (48 hours) and TALL1 (72 hours) treated with 100 nM CompE (black squares) or vehicle only (open circles) plus increasing concentrations of dexamethasone (a); in T-ALL cell lines sensitive to glucocorticoids (DND41, P12 ICHIKAWA) or B-lineage cell lines (b); and in CUTLL1 cells treated with glucocorticoid receptor antagonict RU486 (1 µM) (c) or expressing constitutively active intracellular NOTCH1 (ICN1) (d). (e) Percentage of apoptotic cells (annexinV positive/PI negative) in CUTLL1 (72 hours), KOPTK1 (48 hours) and TALL1 cells (72 hours) treated with DMSO (control), CompE (100 nM), dexamethasone (1 µM) and dexamethasone (1 µM) plus CompE (100 nM). (f-g) Inhibition of apoptosis induction by dexamethatosone plus CompE cotreatment by the z-vad caspase inhibitor as demonstrated by decreased annexinV positive/PI negative cells by flow cytometry (f) and inhibition of PARP cleavage by Western blot (g). Data in (a-f) are means±standard deviation (s.d.) of triplicate experiments. Statistical significance was assessed with Student's t-test.

GSI treatment reverses glucocorticoid resistance in T-ALL. NOTCH1 signaling plays an important role in the specification of cell fate and in the maintenance of cell tropism during T-cell development and in the malignant transformation of T-cell progenitors. These effects are somewhat opposed to that of glucocorticoids, which induce apoptosis in normal and in malignant immature T-cells and therefore have become part of the core treatment for ALL. Indeed, NOTCH1 signaling protects against glucocorticoid-induced cell death in developing thymocytes. These observations suggested that aberrant NOTCH1 signaling might contribute to glucocorticoid resistance in T-ALL and that inhibition of NOTCH signaling with a GSI might sensitize T-ALL cells harboring activating mutations in NOTCH1 to glucocorticoid therapy. To test this hypothesis, the responses of human T-ALL cells to increased doses of dexamethasone in the presence of CompE, a highly active GSI, were analyzed. CUTLL1, a well-characterized T-cell lymphoblastic cell line with activated NOTCH1 is highly resistant to glucocorticoids, showing only a minimal loss of cell viability when treated with dexamethasone concentrations as high as $10^{-5}$ M (FIG. 1a). Treatment of CUTLL1 cells with CompE for 72 hours effectively blocks NOTCH1 signaling and induces a modest cytostatic response characterized by G1 cell cycle arrest with little or no apoptosis. By contrast, treatment of CUTLL1 cells with dexamethasone in the presence of CompE (100 nM) effectively impaired cell viability, with a $IC_{50}$ value of $7.7 \times 10^{-8}$ M at 72 hours for dexamethasone in the presence of CompE (FIG. 1a). Subsequent analysis of KOPTK1 and TALL1, two additional glucocorticoid-resistant T-ALL cell lines that respond with G1 cell cycle arrest upon CompE treatment alone, showed significant decreases in cell viability when treated with both dexamethasone and CompE, indicative of a synergistic interaction between these agents (FIG. 1a). Importantly, analysis of glucocorticoid-sensitive cell lines such as DND41 and P12-ICHIKAWA and diagnostic T-ALL samples, which are typically glucocorticoid-sensitive, showed no evidence of synergistic interaction between CompE and dexamethasone (FIG. 1b and data not shown). Finally, cotreatment of RAMOS and Raji, two B-lineage lymphoma cell lines that lack NOTCH1 signaling, did not affect the sensitivity of these lines to dexamethasone (FIG. 1b).

The synergistic effects of CompE plus dexamethasone observed in CUTLL1 cells were reversed by treatment with RU486, a glucocorticoid receptor antagonist (FIG. 1c). Similarly, expression of an intracellular activated NOTCH1 (ICN1), which does not require gamma-secretase cleavage, bypassed the inhibitory effects of GSIs in NOTCH1 signaling, and protected CUTLL1 cells from the effects of dexamethasone plus CompE cotreatment (FIG. 1d). Together, these data indicate that the synergistic effect of GSI and glucocorticoid treatment in CUTLL1 cells, leading to the reversal of glucocorticoid resistance, is specifically mediated by NOTCH1 inhibition and glucocorticoid receptor activation, and does not merely reflect an acceleration of glucocorticoid cell death.

GSI and glucocorticoid cotreatment induces apoptosis in glucocorticoid-resistant T-ALL cells. The ability of glucocorticoids to efficiently induce programmed cell death in malignant lymphoid cells is an essential component of their anti-leukemic activity. Thus, whether the synergistic effects of CompE and dexamethasone reflect enhanced apoptotic responses to glucocorticoid therapy was considered. Annexin V-PI staining demonstrated increased apoptosis in CUTLL1, KOPTK1, and TALL1 cells treated with CompE and dexamethasone for 48-72 hours (FIG. 1e). Additionally, Western blot analysis of CUTLL1 cells treated with CompE plus dexamethasone showed a marked increase in PARP cleavage, indicative of activation of effector caspases and apoptosis (FIG. 1f). Importantly, no significant increase in PARP cleavage was detected in CUTLL1 cells treated with CompE or dexamethasone alone compared with controls. Furthermore, Z-VAD, a pancaspase inhibitor, reversed the induction of PARP cleavage and apoptosis (detected by annexin V-PI staining) triggered by CompE plus dexamethasone in this cell line (FIGS. 1f,g).

To test whether GSI treatment sensitized T-ALL cells to apoptosis simply by reducing the cell death threshold, the effects of GSI treatment in the response of CUTLL1 cells to a panel of antineoplastic drugs with different mechanisms of action were analyzed. These experiments showed that in contrast to the synergistic effects of CompE and dexamethasone, γ-secretase inhibition did not influence the apoptotic responses triggered by etoposide, vincristine, L-asparaginase or methotrexate in T-ALL (FIG. 7). Similar results were obtained in KOPTK1 and TALL1 cells (data not shown). From these results, it was concluded that GSI treatment sensitizes T-ALL lymphoblasts specifically to glucocorticoid-induced cell death by a mechanism that does not affect the sensitivity of these cells to apoptosis induced by double-strand DNA breaks (etoposide), spindle disfunction (vincristine), inhibition of protein biosynthesis (L-asparaginase), or a block of nucleotide metabolism (methotrexate).

Figure 2:
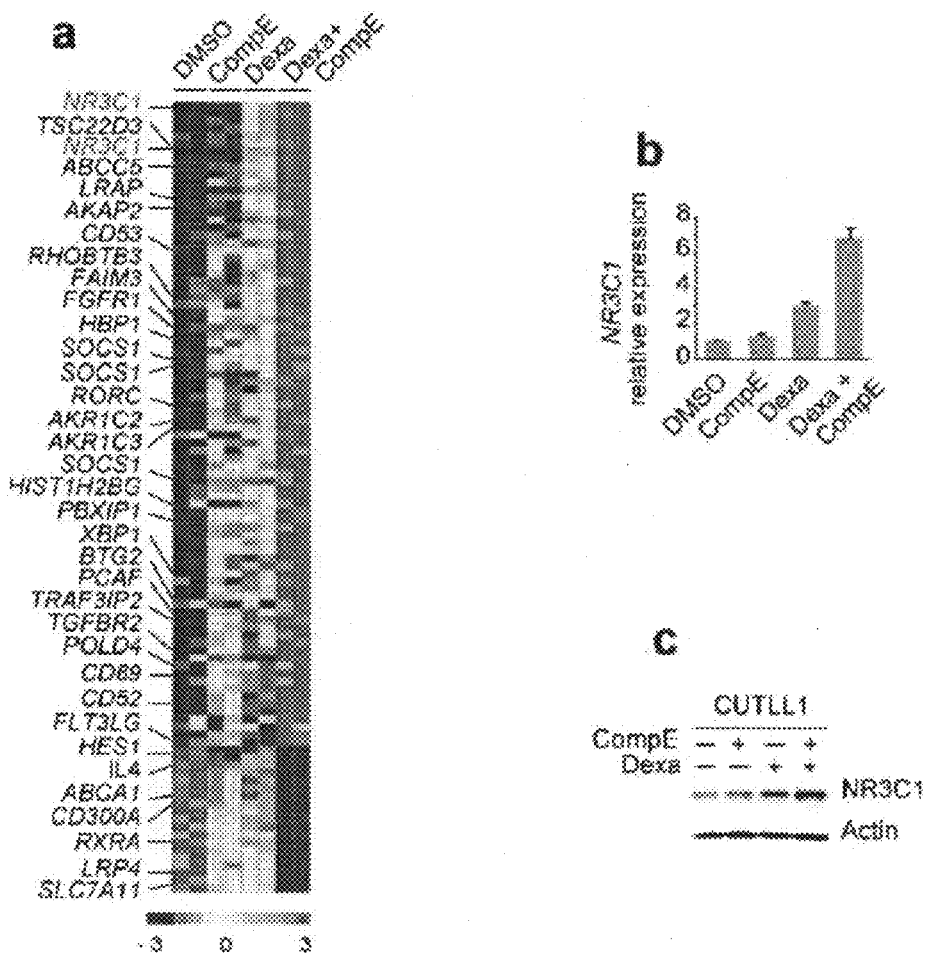
FIG. 2. Inhibition of NOTCH1 signaling restores glucocorticoid receptor autoregulation. (a). Heat map diagram representation of gene expression changes in CUTLL1 cells at 24 hours treated with DMSO, CompE, dexametasone and CompE plus dexametasone. The top 68 synergistically upregulated or downregulated probes upon CompE plus dexametasone cotreatment are shown. Relative expression levels are color coded as indicated in the color bar at the bottom. (b-c) Quantitative RT-PCR analysis of the glucocorticoid receptor gene (NR3C1) (b) and Western blot analysis of glucocorticoid receptor protein levels (c) in CUTLL1 cells treated with dexamethasone and/or CompE compared with vehicle only (DMSO). (d) Apoptosis analysis of CUTLL1 cells infected retroviruses expressing the glucocorticoid receptor (pMSCV NR3C1) or control empty retroviruses (pMSCV puro) upon treatment with CompE, dexamethasone and CompE plus dexamethasone compared with vehicle only (DMSO). (e) Quantitative ChIP analysis of HES1 binding to NR3C1 promoter sequences. TIS: transcription initiation site. (f) Retroviral expression of HES1 (pMSCV HES1) in CUTLL1 cells induces transcriptional upregulation of NR3C1. Expression of a control retrovirus expressing GFP alone (pMSCV GFP) was used as control. (g) Lentiviral shRNA knock-down of HES1 (HES1 shRNA) in CUTLL1 cells induces transcriptional upregulation of NR3C1. Expression of a control shRNA targeting the luciferase gene (shRNA LUC) was used as control. Data in (b) and (d-g) are means±s.d. of triplicate experiments. Statistical significance was assessed with Student's t-test.

Inhibition of NOTCH1 signaling restores glucocorticoid receptor autoregulation. Both NOTCH1 and the glucocorticoid receptor function as ligand activated transcription factors, suggesting that crosstalk between NOTCH1 signaling and glucocorticoid therapy may enhance the transcriptional response to dexamethasone in glucocorticoid resistant T-ALL. To test this possibility, gene expression profiling was performed with oligonucleotide microarrays in CUTLL1 cells treated with vehicle (DMSO), dexamethasone (1 µM), CompE (100 nM) or cotreated with dexamethasone plus CompE for 24 hours. Consistent with previous reports, GSI treatment of CUTLL1 effectively blocked NOTCH1 signaling and induced downregulation of NOTCH1 target genes such as HES1, DTX1 and MYC and a global downregulation of genes involved in growth and metabolism (data not shown). In contrast, dexamethasone treatment induced only moderate changes in the expression of glucocorticoid target genes suggesting a global defect in response to glucocorticoid receptor activation in these cells. Notably, a more efficient glucocorticoid response was observed in cells treated with CompE plus dexamethasone with synergistic upregulation of glucocorticoid regulated genes such as TSC22D3/GILZ, CD53, SOCS1 and BTG2 (FIG. 2a and FIG. 8).

Numerous studies on the mechanisms of glucocorticoid resistance have established that an effective upregulation of the glucocorticoid receptor gene in response to glucocorticoids is required for the activation of apoptosis in human leukemias. Importantly, the glucocorticoid receptor gene (NR3C1) ranked among the top genes synergistically upregulated by dexamethasone plus GSI cotreatment in the microarray analysis (FIG. 2a). Quantitative RT-PCR and Western blot analysis confirmed a marked upregulation of glucocorticoid receptor transcripts and protein in cells treated with dexamethasone plus CompE (FIGS. 2b,c) suggesting that inhibition of NOTCH1 signaling can restore glucocorticoid receptor auto-up-regulation and glucocorticoid sensitivity in otherwise glucocorticoid resistant T-ALL cells. Consistent with this hypothesis, and in agreement with previous reports in T-ALL, retroviral expression of the glucocorticoid receptor gene restored glucocorticoid sensitivity and enhanced the apoptotic response of CUTLL1 cells to dexamethasone (FIG. 2d).

Glucocorticoid receptor auto-up-regulation has been linked to the function of glucocorticoid receptor promoters 1A-hematopoietic- and 1B and 1C ubiquitously expressed. Given the well-established role of NOTCH1 as transcriptional activator, the possibility that HES1, a transcriptional repressor directly controlled by NOTCH1, could mediate the positive effects of NOTCH inhibition in glucocorticoid receptor auto-up-regulation was considered. ChIP-on-chip analysis of promoter occupancy by HES1 in T-ALL cells identified binding of HES1 to regulatory sequences in the glucocorticoid receptor 1B and 1C promoters (FIG. 9). Subsequent quantitative ChIP assays confirmed HES1 binding to glucocorticoid receptor promoters 1B and 1C and demonstrated HES1 binding to regulatory sequences in promoter 1A, which was not covered by the ChIP-on-chip promoter microarray (FIG. 2e). Consistent with these results, retroviral expression of HES1 in CUTLL1 downregulated the expression of the glucocorticoid receptor (FIG. 2f), while HES1 shRNA knock-down resulted in increased glucocorticoid receptor transcript levels (FIG. 2g).

BIM upregulation mediates the reversal of glucocorticoid resistance upon NOTCH1 inhibition in T-ALL. Numerous studies on the mechanisms of action of glucocorticoids have demonstrated an important role of the mitochondrial apoptotic pathway in the activation of glucocorticoid-induced cell death. Thus, it was hypothesized that the reversal of glucocorticoid resistance by NOTCH1 inhibition might involve changes in the expression of critical apoptotic regulators. Analysis of the expression levels of proapotic and antiapoptotic regulators of the mitochondrial cell-death pathway showed that BIM, a BH3-only gene required for glucocorticoid-induced apoptosis, was slightly upregulated by dexamethasone but markedly and synergistically upregulated in CUTLL1 cells treated with dexamethasone plus CompE (FIG. 3a). Similarly, analysis of BMF, a BH3-only gene involved in anoikis/cytoskeletoin stress-induced apoptosis, showed synergistic transcriptional upregulation in cells treated with CompE plus dexamethasone (FIG. 3b). Similar results were obtained in KOPK1 and TALL1 cells (FIG. 10). Western blot analysis demonstrated a marked upregulation of proapoptotic BIM isoforms (BIM EL, L and S) in CUTLL1 cells treated with CompE plus dexamethasone (FIG. 3c). In contrast, changes in BMF gene expression translated to only a moderate increase in BMF protein levels (FIG. 3c). Extended expression analysis of all major apoptosis regulators of the BCL2 and BH3 only subfamilies failed to identify any other significant changes in gene expression potentially associated with an increased cell death response (data not shown).

The upregulation of BIM and BMF in cells treated with dexamethasone plus CompE suggested that these proapototic factors could mediate the reversal of glucocorticoid resistance in T-ALL cells treated with GSIs. Consistent with this prediction, shRNA knock-down of BIM effectively blocked apoptosis induction by CompE plus dexamethasone cotreatment in CUTLL1 cells (FIGS. 3d,e), but downregulation of BMF by shRNA knock-down failed to protect these cells from apoptosis induced by such cotreatment (FIGS. 3f,g). Together, these results demonstrate that BIM upregulation mediates the reversal of glucocorticoid resistance in T-ALL cells treated with dexamethasone plus CompE.

Synergistic antileukemic effects of GSI and GCs in vivo. To test whether the synergistic effects of GSI and glucocorticoid cotreatment in vitro would enhance the therapeutic efficacy of these agents in vivo, the effects of dexamethasone and DBZ, a highly active GSI with established activity in vivo, in a xenograft model of glucocorticoid-resistant T-ALL were analyzed. CUTLL1 cells infected with lentiviruses expressing the luciferase gene were injected subcutaneously in the flanks of immunodeficient (NOD/SCID) mice. After 1 week, animals harboring homogeneous subcutaneous tumors were treated with vehicle only (DMSO), DBZ, dexamethasone or DBZ plus dexamethasone and monitored for 4 days with a bioimaging system to quantify luciferase activity. In this experiment, animals treated with dexamethasone showed progressive tumor growth similar to that observed in vehicle-treated controls, while mice treated with DBZ showed a moderate delay in tumor growth consistent with the cytostatic effect of NOTCH1 inhibition with GSIs observed in CUTLL1 cells in vitro (FIG. 4a-b). By contrast, animals treated with DBZ plus dexamethasone had marked antitumor responses with significant reduction in tumor burden after 4 days of treatment (FIGS. 4a,b; P<0.01). Importantly, tumor xenografts of CUTLL1 cells expressing the activated intracellular form of NOTCH1 (CUTLL1-ICN1) were unresponsive to the combination of DBZ plus dexamethasone (FIG. 4c), indicating that reversal of glucocorticoid resistance in vivo by DBZ treatment is mediated by inhibition of NOTCH1 signaling in the leukemic cells.

To test the significance of these results in a xenograft model that may be a more faithful representation of the natural history of T-ALL patients, CUTLL1 cells expressing the luciferase marker were intravenously injected into irradiated NOD/SCID mice. After 3 weeks, groups of animals with homogeneous tumor burdens were treated with vehicle only, dexamethasone, DBZ or DBZ plus dexamethasone for 2 weeks. Disease progression was readily apparent in control and dexamethasone-treated mice, resulting in tumor-related mortality starting 3 weeks after the initiation of the treatment. By contrast, all animals treated with DBZ plus dexamethasone were disease free three weeks after the initiation of the treatment (FIG. 4d). In this experiment, the GSI-only treatment group showed accelerated mortality associated with weight loss due to GSI toxicity, while mice treated with DBZ plus dexamethasone appeared to be less severely affected. Indeed, with the exception of 2 animals euthanized on day 23 because of excessive (>20%) weight loss, all other mice in this group quickly recovered their baseline body weight in the second week post-treatment. Analysis at the end of the observation period (10 weeks) demonstrated significantly improved survival among mice treated with dexamethasone plus DBZ (P<0.05 vs. controls). Dexamethasone alone lacked an effect on survival, while DBZ was associated with an inferior outcome (P<0.01 vs. controls) due to lethal toxicity. Importantly, all 6 animals treated with DBZ plus dexamethasone were free of leukemia by bioimaging analysis at 8 weeks post-treatment. Furthermore, minimal residual disease levels in this group were below the level of detection as established by flow cytometric analysis of spleen cells after anti-human CD45 staining, confirming complete clearance of human leukemic cells in animals treated with DBZ plus dexamethasone (data not shown).

Glucocorticoid treatment abrogates GSI-induced toxicity in the gut. The improved survival and absence of toxic deaths among leukemia-bearing mice treated with DBZ plus dexamethasone compared with mice treated with GSI alone suggested that glucocorticoid therapy ameliorates the gastrointestinal toxicity typically associated with GSI treatment. To test this hypothesis, the histologic changes in the intestines of C57/Bl6 mice treated with dexamethasone, DBZ or dexamethasone plus DBZ, compared to vehicle-only controls, were analyzed. In contrast to animals treated with dexamethasone, whose findings were similar to controls (FIG. 5 and FIG. 11), DBZ-treated animals had severe intestinal secretory metaplasia characterized by a marked increase in the number of goblet cells and arrested cell proliferation (determined by Ki67 immunostaining) in the crypts of the small intestine (FIG. 5 and FIG. 11). Importantly, mice cotreated with DBZ plus dexamethasone showed normal goblet cell numbers with preservation of the architecture and proliferation of the intestinal epithelium (FIG. 5 and FIG. 11).

Further histologic analysis of the thymus and spleen revealed marked differences in treatment effects (FIG. 11). Thymic atrophy was more severe in animals treated with DBZ plus dexamethasone than in those receiving either agent alone. In the spleen, DBZ induced disappearance of the marginal zone in the white pulp, a defect typically associated with loss of NOTCH signaling. Mice treated with dexamethasone showed moderate atrophy of the white pulp with preservation of the marginal zone and disorganization of the red pulp. By contrast, dexamethasone plus DBZ produced severe alterations of the splenic architecture, characterized by marked lymphoid atrophy and disappearance of the marginal zone in the white pulp and prominent disorganization of the red pulp (FIG. 11). Importantly, these effects of dexamethasone plus DBZ treatment in lymphoid tissues were reversible as demonstrated by restored organ size and cellullarity with complete repletion of double positive T-cells and marginal zone B cells in the thymus and the spleen, respectively (FIGS. 12 and 13).

Pharmacokinetic analysis of mice treated with dexamethasone for 5 days showed that glucocorticoid treatment reduced the clearance of DBZ in vivo (FIG. 14). Further analysis of drug metabolism in vitro showed a decrease in DBZ metabolism by liver microsomes induced by dexamethasone (FIG. 14). These results strongly suggest that the reversal of GSI-induced gastrointestinal toxicity by dexamethasone is not mediated by changes in drug metabolism, but by a protective effect of glucocorticoids in the intestinal epithelium.

Regulation of Klf4 expression by NOTCH and glucocorticoids in GSI induced gut toxicity. The tumor suppressor Klf4 is a transcription factor expressed in goblet cells and goblet cell precursors that negatively regulates cell proliferation in the gut and is essential for the differentiation of intestinal stem cells to secretory cells. NOTCH inhibition with GSIs mimics the effects of Klf4 activation in the gut, suggesting that NOTCH signaling and glucocorticoids could interact by differentially regulating Klf4 expression. To test this hypothesis, the expression of Klf4 in the intestines of mice treated with vehicle only (DMSO), dexamethasone, DBZ or DBZ plus dexamethasone, was analyzed. Notably, analysis of KLF4 expression by immunohistochemistry showed nuclear staining in goblet cells in the villi and in scattered cells corresponding to goblet cell precursors in the crypt of control animals; reduced KLF4 expression in dexamethasone treated mice; a marked increased in KLF4 staining in the crypt and villi of GSI treated mice; which was reduced to levels equivalent to those found in control mice in the group cotreated with dexamethasone plus GSI (FIGS. 6a,b). Similarly, RT-PCR analysis showed that NOTCH inhibition with DBZ led to a gradual increase of Klf4 expression in the gut, whereas the intestinal epithelia of animals treated with dexamethasone or dexamethasone plus DBZ showed decreased and stable expression of Klf4, respectively (FIG. 6c). Consistent with these results, luciferase reporter assays demonstrated that both activation of NOTCH signaling by ICN1 or expression of HES1 in AGS cells downregulate the activity of the KLF4 promoter (FIG. 6d). Furthermore, chromatin immunoprecipitation in HT29 cells and shRNA knock-down of HES1 in AGS cells demonstrated binding of HES1 protein to the KLF4 promoter and upregulation of KLF4 transcripts, respectively (FIGS. 6 e,f). Overall, these experiments support a mechanistic role for Klf4 upregulation in GSI induced gut toxicity and suggest that protection from GSI-induced gut metaplasia by dexamethasone is mediated by downregulation of Klf4 expression, which antagonizes the effects of GSI treatment on the NOTCH-HES1-KLF4 regulatory axis.

Treatments that target the aberrant signaling pathways controlling the growth and survival of malignant T-lymphoblasts are attracting wide attention as promising tools in the therapeutic armamentarium for human leukemias. The rationale for inhibiting oncogenic pathways in anticancer therapy is based on the concept of oncogene addiction, which posits that cancer cells become dependent on continuous oncogenic signals for proliferation and survival, but also on experimental evidence linking oncogenic pathways with chemotherapy resistance. Thus, the combination of molecularly targeted drugs with conventional antileukemic agents could provide an improved therapeutic window with increased efficacy and reduced toxicity.

The foregoing examples substantiate this prediction, showing that inhibition of NOTCH1 signaling can effectively abrogate glucocorticoid resistance in T-ALL. Furthermore, the combination of glucocorticoids with GSIs was strongly synergistic, shifting the effects of GSI treatment from mildly cytostatic to strongly cytotoxic. The synergistic effects of GSI-induced NOTCH1 inhibition and glucocorticoids were mediated by improved glucocorticoid receptor auto-up-regulation, leading to effective upregulation of BIM, a proapoptotic BH3-only factor previously implicated in glucocorticoid-induced cell death. Notably, changes in MCL1 protein levels in cells treated with CompE plus dexamethasone (data not shown) were not detected, despite post-transcriptional downregulation of this antiapototic factor has been shown to mediate the reversal of glucocorticoid resistance in leukemic lymphoblasts upon inhibition of mTOR signaling with rapamycin. Similarly, changes were not observed in the differentiation arrest of our T-ALL cells that could be linked to differential glucocorticoid sensitivity, or transcriptional changes in the SRG3 gene (data not shown), mechanisms proposed to reduce the sensitivity to glucocorticoid induced apoptosis downstream of NOTCH1 activation in mouse primary thymocytes.

Furthermore, as described above, in vivo studies using a mouse xenograft model of T-ALL demonstrated an increased antitumor effect in animals treated with both agents, validating the in vitro results and supporting a role for the glucocorticoid-GSI combination in clinical settings. Surprisingly, there was also a marked reduction in the gastrointestinal toxicity induced by GSIs. Pharmakocinetic analysis demonstrated that the reduced toxicity in animals treated with dexamethasone plus DBZ did not result from glucocorticoid-induced changes in DBZ metabolism.

Also as described above, histologic analysis showed an almost complete reversal of the proliferative arrest and the intestinal secretory metaplasia typically induced by GSI treatment in mice cotreated with a glucocorticoid (dexamethasone) and a GSI (DBZ). Importantly, although combined treatment with dexamethasone plus DBZ resulted in increased lymphoid depletion in the thymus and the spleen, these changes were not associated with any clinical symptoms in this group and were completely reversible.

Cell fate decisions in the gut are regulated by a coordinated network of transcription factors that drive the differentiation of intestinal progenitors toward different outcomes. In this context, Klf4 is a critical regulatory factor in the differentiation of intestinal stem cells to secretory goblet cells. The opposing effects of GSIs (upregulation) and glucocorticoids (downregulation) in KLF4 expression suggests that dexamethasone-induced downregulation of Klf4 expression may mediate the enteroprotective effect of glucocorticoids against GSI-induced gut toxicity.

Despite the strong rationale for inhibiting NOTCH1 signaling for the treatment of T-ALL harboring activating mutations in the NOTCH1 gene, progress in clinical testing of GSIs has been halted by the lack of effective antileukemic cytotoxicity and the development of severe gastrointestinal toxicity. The foregoing examples demonstrate that combination therapy with GSIs plus glucocorticoids is highly effective against glucocorticoid-resistant T-ALL both in vitro and in vivo. In addition, the protective effect of glucocorticoids against GSI-induced gut toxicity demonstrates the feasibility of pharmacologic strategies to ameliorate the toxicity of these drugs. This raises the intriguing possibility that coadministration of a glucocorticoid targeting the gastrointestinal tract, but lacking systemic effects (e.g., oral busesonide), could eliminate a major obstacle to the clinical application of GSIs in Alzheimer's disease, where chronic inhibition of γ-secretase is needed to block the production of amyloidogenic Aβ peptides.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for reducing, treating, or ameliorating a side-effect of a NOTCH-1 inhibitor in a patient with cancer, which method comprises administering to the patient an effective amount of a glucocorticoid.

2. The method according to claim 1, wherein the cancer is a lymphoid malignancy.

3. The method according to claim 2, wherein the cancer is T-cell lymphoblastic leukemia (T-ALL) or lymphoma.

4. The method according to claim 1, wherein the glucocorticoid is selected from the group consisting of cortisol, budesonide, hydrocortisone, dexamethasone, prednisone, prednisolone, methylprednisolone and combinations, enantiomers, optical isomers, diastereomers, N-oxides, crystalline forms, hydrates, metabolites or pharmaceutically acceptable salts thereof.

5. The method according to claim 1, wherein the NOTCH-1 inhibitor is a γ-secretase inhibitor (GSI).

6. The method according to claim 5, wherein the GSI is selected from the group consisting of [(2S)-2-{[(3,5-Difluorophenyl)acetyl]amino}-N-[(3S)1-methyl-2-oxo-5-phenyl-2,3-dihydro-1H-1,4-benzodiazepin-3-yl] propanamide] (CompE), N-[N-(3,5-difluorophenacetyl)-L-alanyl]-Sphenylglycine-t-butylester (DAPT), LY411575, (5S)-(t-Butoxycarbonylamino)-6-phenyl-(4R)hydroxy-(2R)benzylhexanoyl)-L-leu-L-phe-amide (L-685,458), L-852,647, MW167, WPE-III-31, LY450139,MRK003, R-flurbiprofen ([1,1'-Biphenyl]-4-acetic acid, 2-fluoro-alpha-methyl), NGX-555, E2012, Begacestat (2-Thiophenesulfonamide, 5-chloro-N-[(1S)-3,3,3-trifluoro-1-(hydroxymethyl)-2-(trifluoromethyl)propyl]-), NIC5-15, and CHF-5074 and pharmaceutically acceptable salts, and combinations thereof.

7. The method according to claim 1, wherein the NOTCH-1 inhibitor is [(2S)-2-{[(3,5-Difluorophenyl)acetyl]amino}-N-[(3S)1-methyl-2-oxo-5-phenyl-2,3-dihydro-1H-1,4-benzodiazepin-3-yl] propanamide] (CompE) or a pharmaceutically acceptable salt thereof and the glucocorticoid is dexamethasone or a pharmaceutically acceptable salt thereof.

8. A method for reducing, treating, or ameliorating the effects of intestinal secretory metaplasia caused by a NOTCH-1 inhibitor in a patient with cancer, which method comprises administering to the patient an effective amount of a glucocorticoid.

9. The method according to claim 8, wherein the cancer is a lymphoid malignancy.

10. The method according to claim 9, wherein the cancer is T-cell lymphoblastic leukemia (T-ALL) or lymphoma.

11. The method according to claim 8, wherein the glucocorticoid is selected from the group consisting of cortisol, budesonide, hydrocortisone, dexamethasone, prednisone, prednisolone, methylprednisolone and combinations, enantiomers, optical isomers, diastereomers, N-oxides, crystalline forms, hydrates, metabolites or pharmaceutically acceptable salts thereof.

12. The method according to claim 8, wherein the NOTCH-1 inhibitor is a γ-secretase inhibitor (GSI).

13. The method according to claim 12, wherein the GSI is selected from the group consisting of [(2S)-2-{[(3,5-Difluorophenyl)acetyl]amino}-N-[(3S)1-methyl-2-oxo-5-phenyl-2,3-dihydro-1H-1,4-benzodiazepin-3-yl] propanamide] (CompE), N-[N-(3,5-difluorophenacetyl)-L-alanyl]-S-phenylglycine-t-butylester (DAPT), LY411575, (5S)-(t-Butoxycarbonylamino)-6-phenyl-(4R)hydroxy-(2R)benzylhexanoyl)-L-leu-L-phe-amide (L-685,458), L-852,647, MW167, WPE-III-31, LY450139, MRK003, R-flurbiprofen ([1,1'-Biphenyl]-4-acetic acid, 2-fluoro-alpha-methyl), NGX-555, E2012, Begacestat (2-Thiophenesulfonamide, 5-chloro-N-[(1S)-3,3,3-trifluoro-1-(hydroxymethyl)-2-(trifluoromethyl)propyl]-), NIC5-15, and CHF-5074 and pharmaceutically acceptable salts, and combinations thereof.

14. The method according to claim 8, wherein the NOTCH-1 inhibitor is [(2S)-2-{[(3,5-Difluorophenyl)acetyl]amino}-N-[(3S)1-methyl-2-oxo-5-phenyl-2,3-dihydro-1H-1,4-benzodiazepin-3-yl] propanamide] (CompE) or a pharmaceutically acceptable salt thereof and the glucocorticoid is dexamethasone or a pharmaceutically acceptable salt thereof.

* * * * *